United States Patent
Rodriguez et al.

(10) Patent No.: US 7,832,295 B2
(45) Date of Patent: Nov. 16, 2010

(54) SUBMERSIBLE PROBE APPARATUS FOR AQUEOUS ENVIRONMENT MONITORING WITH NEW CAM-TWIST INTERCONNECT, LIQUID BARRIER, AND BATTERY PACK

(75) Inventors: Dustin S. Rodriguez, Fort Collins, CO (US); Bruce A. Barker, Fort Collins, CO (US); Duane B. McKee, Fort Collins, CO (US)

(73) Assignee: In-Situ, Inc., Fort Collins, CO (US)

( * ) Notice: Subject to any disclaimer, the term of this patent is extended or adjusted under 35 U.S.C. 154(b) by 341 days.

(21) Appl. No.: 11/884,352

(22) PCT Filed: Feb. 14, 2006

(86) PCT No.: PCT/US2006/005102

§ 371 (c)(1),
(2), (4) Date: Aug. 14, 2007

(87) PCT Pub. No.: WO2006/088829

PCT Pub. Date: Aug. 24, 2006

(65) Prior Publication Data

US 2008/0141797 A1    Jun. 19, 2008

Related U.S. Application Data

(60) Provisional application No. 60/653,452, filed on Feb. 15, 2005, provisional application No. 60/671,303, filed on Apr. 14, 2005.

(51) Int. Cl.
*G01N 33/18* (2006.01)
*G01D 11/00* (2006.01)

(52) U.S. Cl. .................. 73/866.5; 73/53.01; 73/170.29

(58) Field of Classification Search ............... 73/53.01, 73/170.29, 170.33–170.34, 866.5
See application file for complete search history.

(56) References Cited

U.S. PATENT DOCUMENTS 3,214,964 A  *  11/1965  Davis ..................... 73/53.01

(Continued)

OTHER PUBLICATIONS

European Application No. 06 734 983.7 Invitation pursuant to Rule 62a(1) EPC dated Apr. 21, 2010, 2 pages.

(Continued)

*Primary Examiner*—Thomas P Noland
(74) *Attorney, Agent, or Firm*—Lathrop & Gage LLP

(57) ABSTRACT

A submersible water monitoring probe assembly including: a cam-twist type interconnect mechanism; flexible PCBA (printed circuit board assembly) having flexible ribbon cable sandwiched between layers of an elongated circuit board, the ribbon cable extending outwardly from each end of the board and along an elongated probe-body; internal gas-permeable and generally liquid impermeable barrier assembly disposed within the cam-twist inter-connect mechanism between the elongated PCBA housed within the probe-body and an electrical connector of the cam-twist interconnect mechanism; and if used, a vented cable assembly, or other means of transmitting sensor data collected by sensing circuitry within a submersed probe-end. Also, an extender assembly for use with the submersible probe. At each end portion of the extender assembly is either a male cam-twist type interconnect piece or a female cam-twist type interconnect piece. The length-extender assembly may be electrically adapted to house one or more battery cells.

23 Claims, 14 Drawing Sheets

U.S. PATENT DOCUMENTS

| | | | | |
|---|---|---|---|---|
| 3,469,444 | A * | 9/1969 | Ayer | 73/170.34 |
| 5,356,593 | A * | 10/1994 | Heiberger et al. | 422/45 |
| 5,821,405 | A * | 10/1998 | Dickey et al. | 73/53.01 |
| 6,007,034 | A * | 12/1999 | Stoll et al. | 73/866.5 X |
| 6,065,359 | A * | 5/2000 | Takanashi et al. | 73/866.5 |
| 6,463,818 | B1 * | 10/2002 | Stagg et al. | 73/866.5 |
| 6,640,658 | B1 * | 11/2003 | Guerrero et al. | 73/866.5 |
| 6,774,623 | B2 * | 8/2004 | Palfenier et al. | 73/866.5 X |
| 6,798,347 | B2 * | 9/2004 | Henry et al. | 340/680 |
| 2003/0047014 | A1 * | 3/2003 | Stagg et al. | 73/866.5 |
| 2004/0074324 | A1 * | 4/2004 | McVicar | 73/866.5 |
| 2007/0013381 | A1 * | 1/2007 | Biberger | 73/53.01 X |

OTHER PUBLICATIONS

Canadian Application No. 2,597,917, Office Action dated May 17, 2010, 2 pages.

* cited by examiner

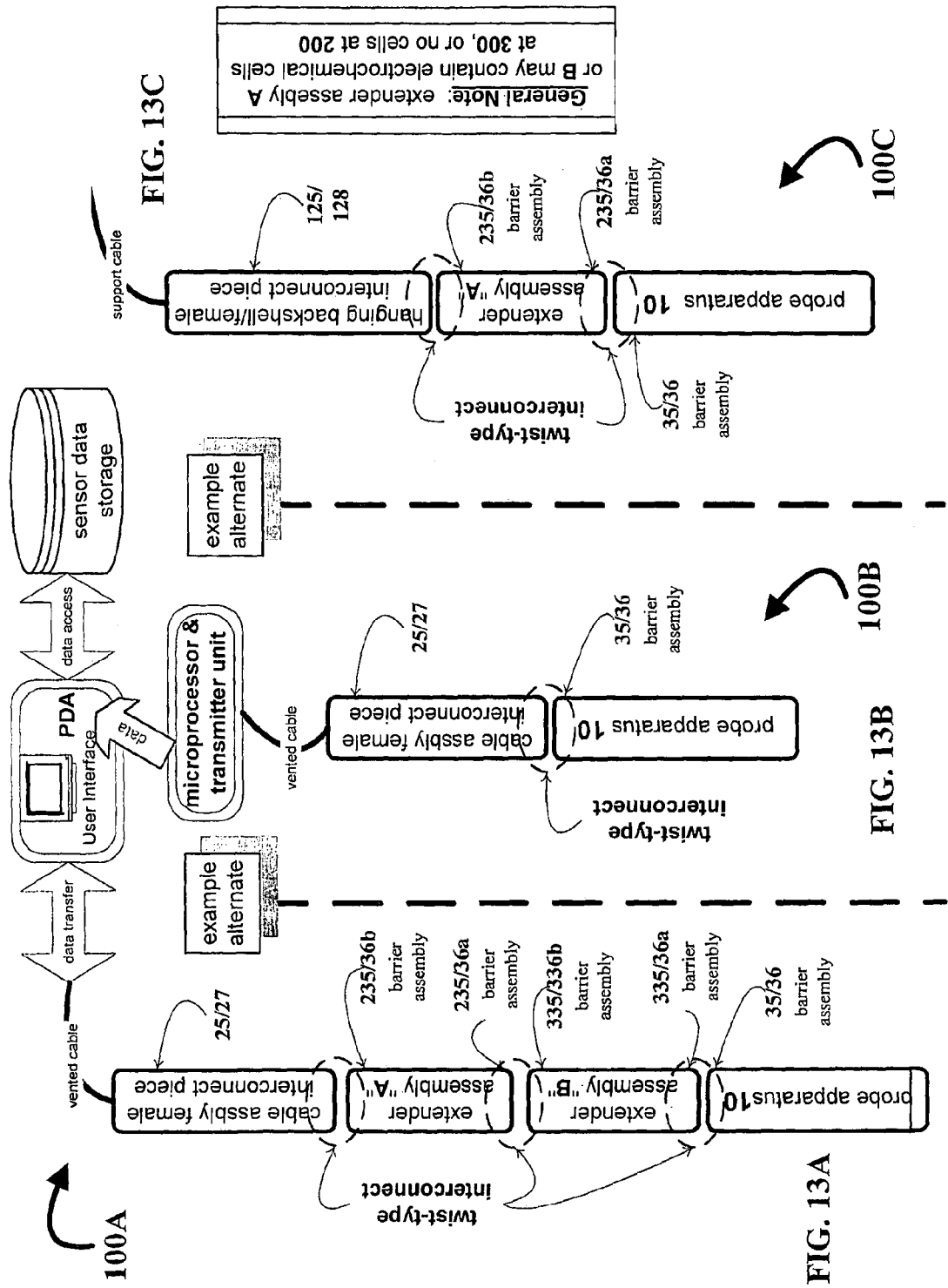

SUBMERSIBLE PROBE APPARATUS FOR AQUEOUS ENVIRONMENT MONITORING WITH NEW CAM-TWIST INTERCONNECT, LIQUID BARRIER, AND BATTERY PACK

Commonly owned by assignee-applicant hereof are provisional patent apps. U.S. App. No. 60/653,452 filed 15 Feb. 2005 and U.S. App. No. 60/671,303 filed 14 Apr. 2005, having at least one common inventor hereof, to which priority is claimed herein.

BACKGROUND OF THE INVENTION

Field of the Invention

In general, the present invention relates to probes for on-site 'down-hole' monitoring of bodies of water (wells, aquifers, lakes, rivers, streams, ocean water, etc.) to collect information/data concerning wafer level (measuring pressure), temperature, and other such parameters. Water monitoring probes of this type, including those designed and manufactured by the assignee hereof, are intended for long term monitoring and are connected to a vented cable assembly, at least a portion of which is also submersed within the body of water. The vented cable assembly operates as a data communications pathway for transmitting information about the measured parameters to a separate processing unit. A vented cable assembly is not required, however. The probe may be used without a vented cabling assembly, for example where absolute pressure is being measured and, thus, no need to measure pressure difference within the water and the above-surface atmospheric pressure. In this case—where above-surface pressure is not factored into a reading—a metal cover piece referred to as a 'hanging backshell' is connected to the metal probe housing by way of mating threaded sections. Sturdy cabling can then be connected to the backshell (e.g., threaded through, or hooked/clipped to, a hole or hook in the hanging backshell piece) so that the probe can be lowered into a submersed position for monitoring.

More particularly, this disclosure is directed to a new submersible water monitoring probe assembly including: a cam-twist type interconnect mechanism; flexible PCBA (printed circuit board assembly)—sometimes referred to as PWA (printed wiring assembly)—having flexible ribbon cable sandwiched between layers of an elongated circuit board, the ribbon cable extending outwardly from each end of the board and along an elongated probe-body; internal gas-permeable and generally liquid impermeable barrier assembly disposed within the cam-twist interconnect mechanism between the elongated PCBA housed within the probe-body and an electrical connector of the cam-twist interconnect mechanism; and if used, a vented cable assembly, or other means of transmitting sensor data collected by sensing circuitry within a submersed probe-end. The flexible ribbon cable extending from each end of the elongated circuit board is used for electrically connecting an internal power source (e.g., long-life Lithium battery), to sensor circuitry at the submersed data collection end of the probe, and to an electrical connector within the cam-twist type interconnect mechanism. Through the electrical connector, electrical communication may be established between the PCBA and the data transmission pathway employed (such as vented cable assembly, data cable connector, or backshell). By way of example, only, the electrical connector may be any suitable such as a LEMO® brand connector—preferably one that is keyed via half-moon or otherwise as shown herein, LEMO® connectors are distributed by LEMO USA Inc.

As will be described hereafter, the unique design of the cam-twist type interconnect mechanism permits handy connection and exchange of either a vented cable assembly (FIGS. 6A-D and 7A-B), a backshell piece (FIGS. 8A-B), or either end of a novel extender assembly (FIGS. 10A-D, and FIGS. 11A-D) the latter of which is shown adapted for housing one or more battery cells/packs. The sensor data collected is initially processed and stored 'on-board' the probe by the PCBA for later communication to an external computer processing unit (e.g., handheld, laptop, desktop, etc.) via a vented cable assembly, a data transmitter (for example, if a backshell is used, the backshell may be equipped with a radio frequency, RF, or infra-red, IR, transmitter/port), or a data transmission cable may be connected to the probe body once the probe is pulled from its monitoring position.

As mentioned above, a unique extender assembly for use with a submersible probe apparatus for monitoring aqueous environments is also described. Preferably at each end portion of the extender assembly (such as that at 200 in FIGS. 10A-D, at 300 in FIGS. 11A-D, at 200' in FIG. 12A, and at 300' in FIG. 12B) is a portion of a cam-twist type interconnect piece, either a male interconnect piece (e.g., 245*a/b*, 345*a/b* in FIGS. 10D and 11D) or a female interconnect piece (e.g., as labeled 25'/27' in FIG. 12A, and 25"/27" in FIG. 12B) with features structurally similar to those labeled 45 and 25/27 throughout. The length-extender assembly (FIGS. 10A-D, 12A) may be electrically adapted to house one or more battery cells (e.g., as shown in FIGS. 11A-D, 12B). Further unique features of the extender assembly will be appreciated in connection with the more-detailed description below.

Assignee's Earlier Work in Water Level/Pressure and Water Quality Monitoring Probes.

The assignee hereof also owns U.S. Pat. No. 6,798,347 B2 issued on 28 Sep. 2004 to Henry et al (entitled Sensor Head Component). This patent describes an earlier probe design and is fully incorporated herein by reference to the extent it provides supportive technological details and information of the aqueous environment in which the unique probe device of the invention may be operated as well as the system of components used for water monitoring (e.g., the elongated probe assembly, a cable assembly, electrical connectors, PDA or other suitable portable or fixed computerized unit for processing data/information). The focus of these earlier design efforts by the assignee were on portability: Traditional alkaline batteries were used to power a printed circuit board (PCB) using traditional electrical connectors and wiring soldered to the PCB, all within a stainless steel probe housing tube, as further set forth in the assignee's manual for its earlier-generation MiniTROLL® water monitoring probe.

Glossary of Miscellaneous Terms Provided by Way of Background Reference, Only:

Wireless. A term used to describe communications in which electromagnetic waves (rather than some form of wire or cabling) carry the signal over part or the entire communication, or transmission pathway, between transmitter and receiver considered 'remote' from one another (i.e., not in physical contact).

SUMMARY OF THE INVENTION

Briefly described, once again, the invention is a submersible probe apparatus 10 for monitoring parameters within an aqueous environment such as bodies of water (wells, aquifers, lakes, rivers, streams, ocean water, and so on) to collect information/data concerning water level (measuring pressure), temp., and other parameters. One will appreciate the many distinguishable structural features of the probe apparatus described herein from those of conventional water monitoring probes, including prior probe designs owned by the assignee to this application. Certain of the unique features of the invention, and further unique combinations of features—as supported and contemplated herein—provide a variety of advantages, among which include one or more of the following: (a) Structural design flexibility/versatility; (b) ongoing, reliable monitoring without disruption of the aqueous environment undergoing monitoring; and (c) handy integration into equipment/systems currently in use to monitor aqueous environments.

BRIEF DESCRIPTION OF FIGURES

For purposes of illustrating the innovative nature plus flexibility of design and versatility of the invention the following figures are included. One can readily appreciate the advantages and the many features that distinguish the instant invention from conventional/currently available water monitoring probes. The figures have been included to communicate the features of applicants' innovative apparatus and system features by way of example, only, and are in no way intended to unduly limit the disclosure hereof. Briefly, consecutively labeled figures include:

FIGS. 13A-13C are high-level schematics depicting a few of the many possibilities contemplated hereby, of alternate configurations of components comprising a probe apparatus, such as that at 10, and extender assemblies, such as those labeled 200, 300, 200', and 300' throughout, by way of example only.

DESCRIPTION DETAILING FEATURES OF THE INVENTION

By viewing the figures which depict representative structural embodiments of a probe apparatus of the invention, one can further appreciate the unique nature of core as well as additional and alternative features that are within the spirit and scope of this technical discussion. Reference will be made back-and-forth to features depicted in the various embodiments, as illustrated in various figures. As one will appreciate, the high-level schematics in FIGS. 13A-C depict alternate configurations of component combinations comprising a probe apparatus, such as that labeled 10 throughout, with the unique extender assembly, such as those labeled 200, 300, 200', and 300' throughout, and depicted herein by way of example only.

Figure 1:
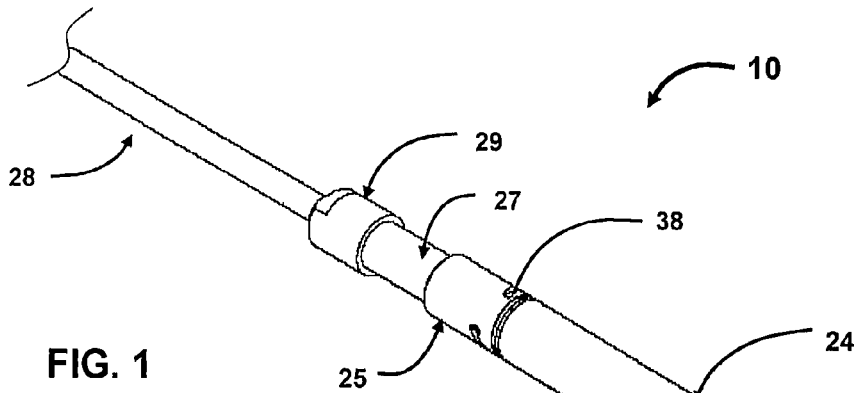
FIG. 1 is an isometric of a monitoring probe apparatus 10 of the invention.
Figure 2A:
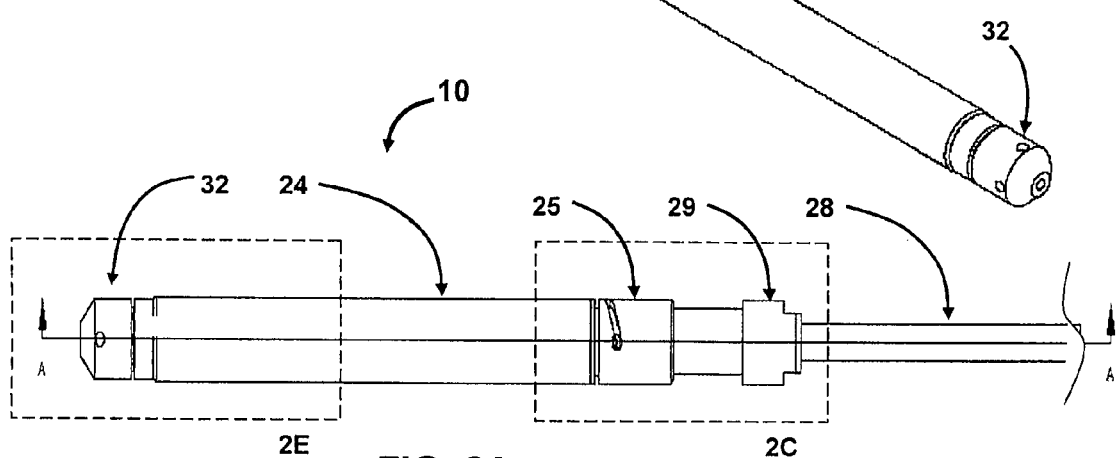
FIG. 2A is a side plan view of the probe apparatus 10 in FIG. 1.
Figure 2B:
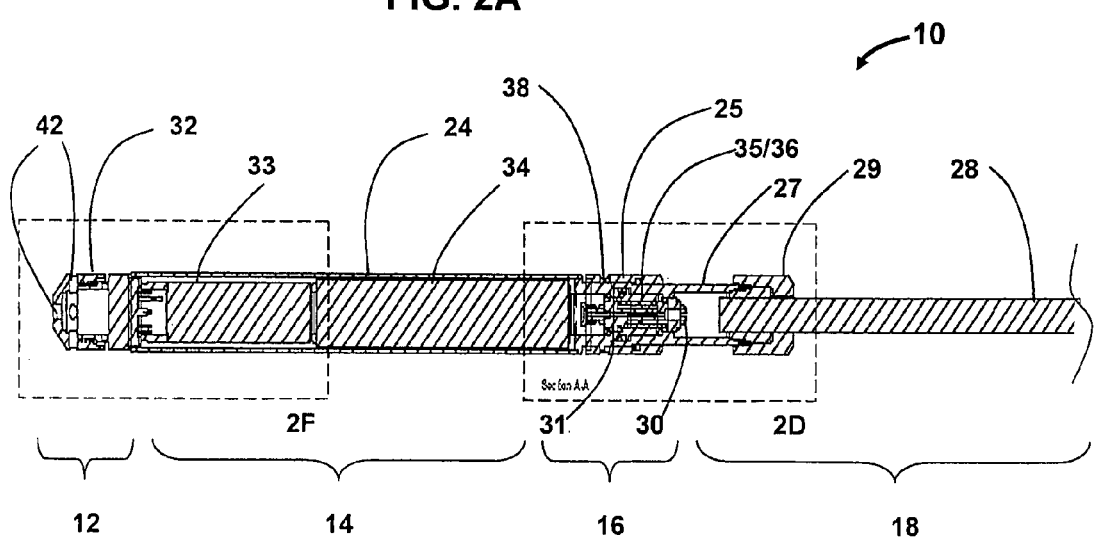
FIG. 2B is a sectional view taken along A-A of FIG. 2A of the probe 10.
Figure 2C:
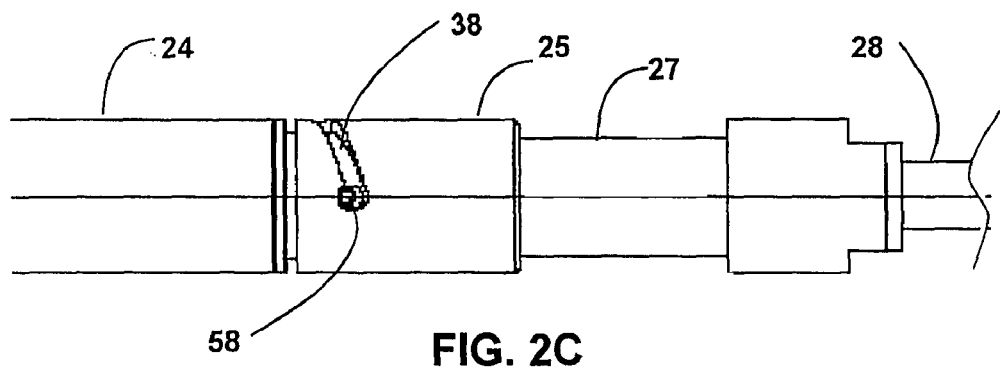
FIG. 2C is an enlarged side plan view of probe 10 within box 2C of FIG. 2A.
Figure 2D:
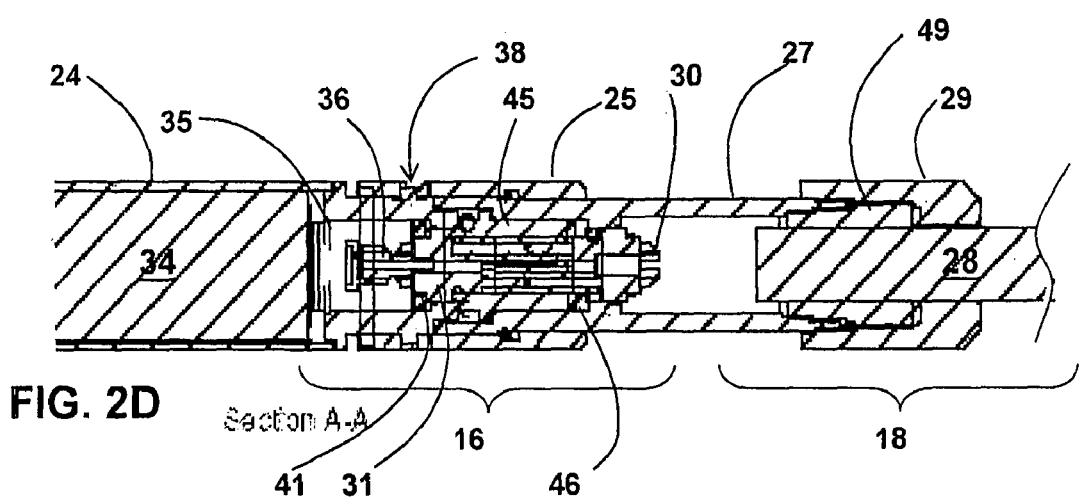
FIG. 2D is an enlarged sectional view of the section of probe 10 shown in FIG. 2C and as outlined within box 2D of FIG. 2B.
Figure 2E:
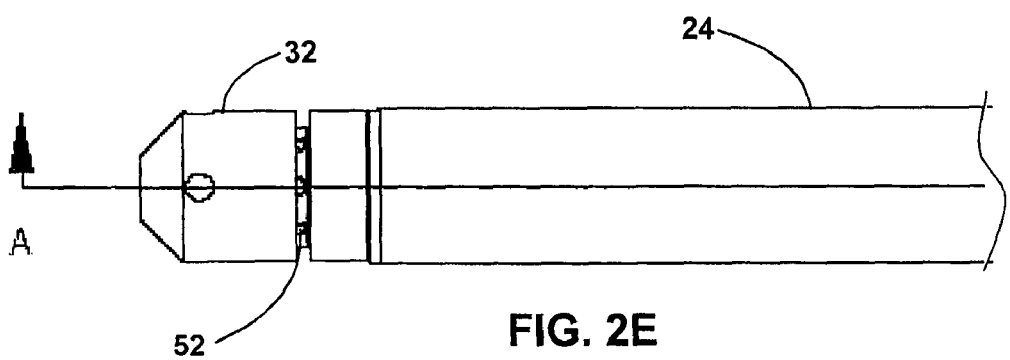
FIG. 2E is an enlarged side plan view of probe 10 within box 2E of FIG. 2A.
Figure 2F:
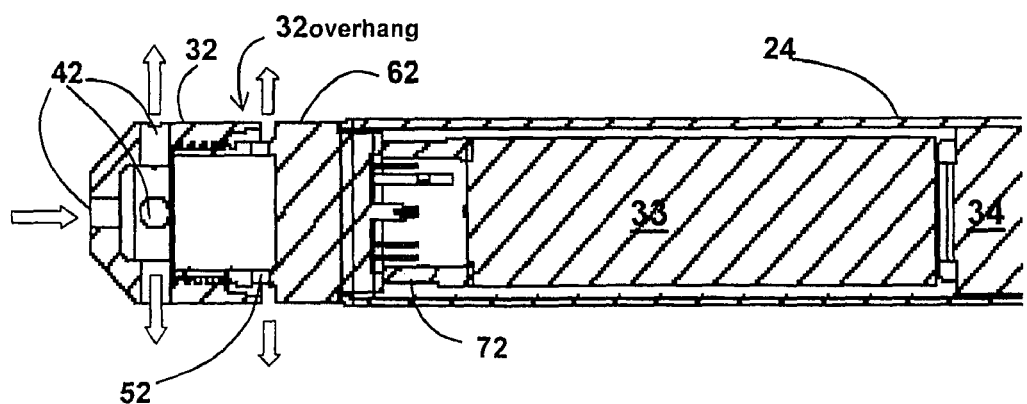
FIG. 2F is an enlarged sectional view of the section of probe 10 shown in FIG. 2E and as outlined within box 2F of FIG. 2B.
Figure 3:
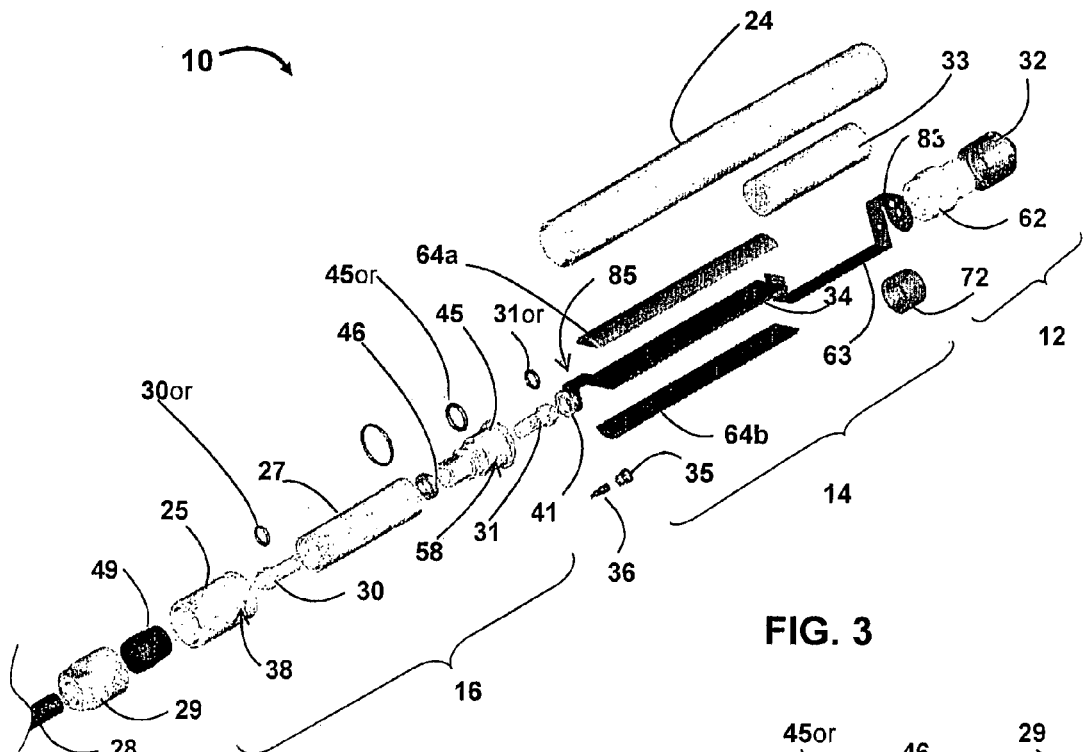
FIG. 3 is an isometric exploded assembly of probe apparatus 10.

Once again, for handy reference in connection with the following detailed discussion: FIG. 1 is an isometric of a monitoring probe apparatus 10 of the invention, FIG. 2A is a side plan view thereof, with FIG. 2B as a sectional view taken along A-A of FIG. 2A. FIG. 2C is an enlarged side plan view of probe 10 within box 2C of FIG. 2A. FIG. 2D is an enlarged sectional view of the section of the probe in FIG. 2C as outlined within box 2D of FIG. 2B. FIG. 2E is an enlarged side plan view of probe 10 within box 2E of FIG. 2A. FIG. 2F is an enlarged sectional view of the section of probe 10 shown in FIG. 2E and as outlined within box 2F of FIG. 2B. FIG. 3 is an isometric exploded assembly of probe apparatus 10.

Figure 4A:
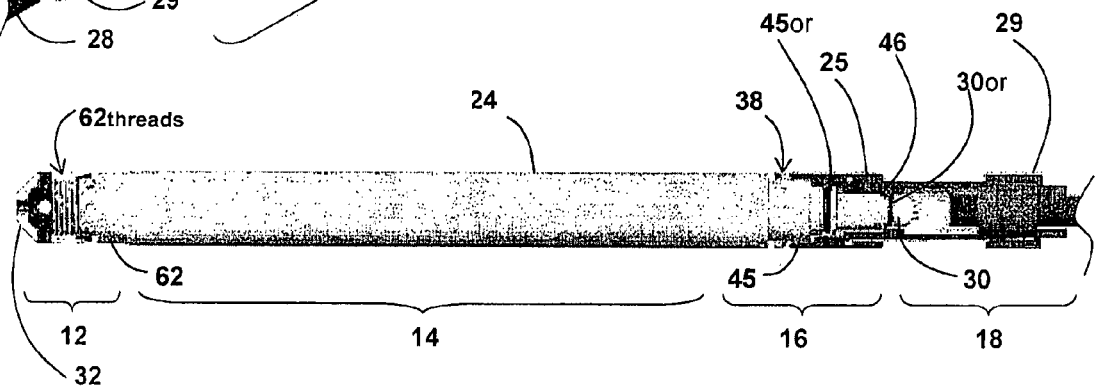
FIG. 4A is a side plan view of an assembled probe apparatus 10 whereby certain features of probe sections labeled 12, 16, 18 have been removed and/or depicted in cross-section fashion to show interior details.
Figure 4B:
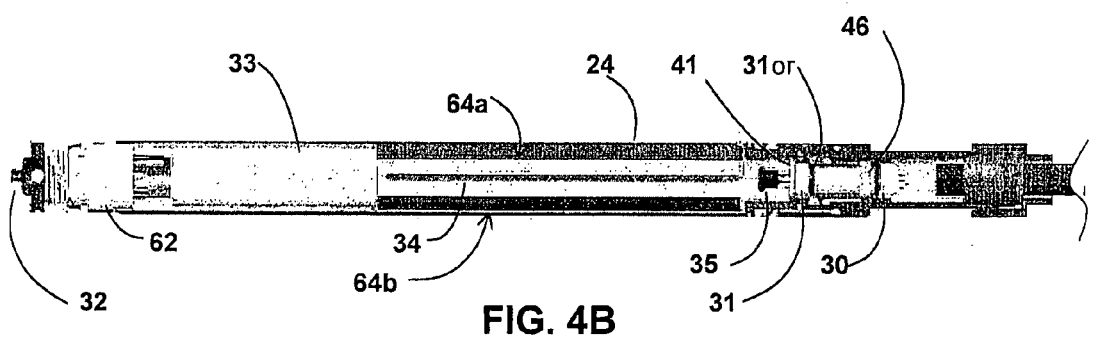
FIG. 4B is a side plan view of the assembled probe apparatus 10 of FIG. 4A whereby certain features of probe mainbody section 14 have been removed and/or depicted in cross-section fashion to show interior details.
Figure 5A:
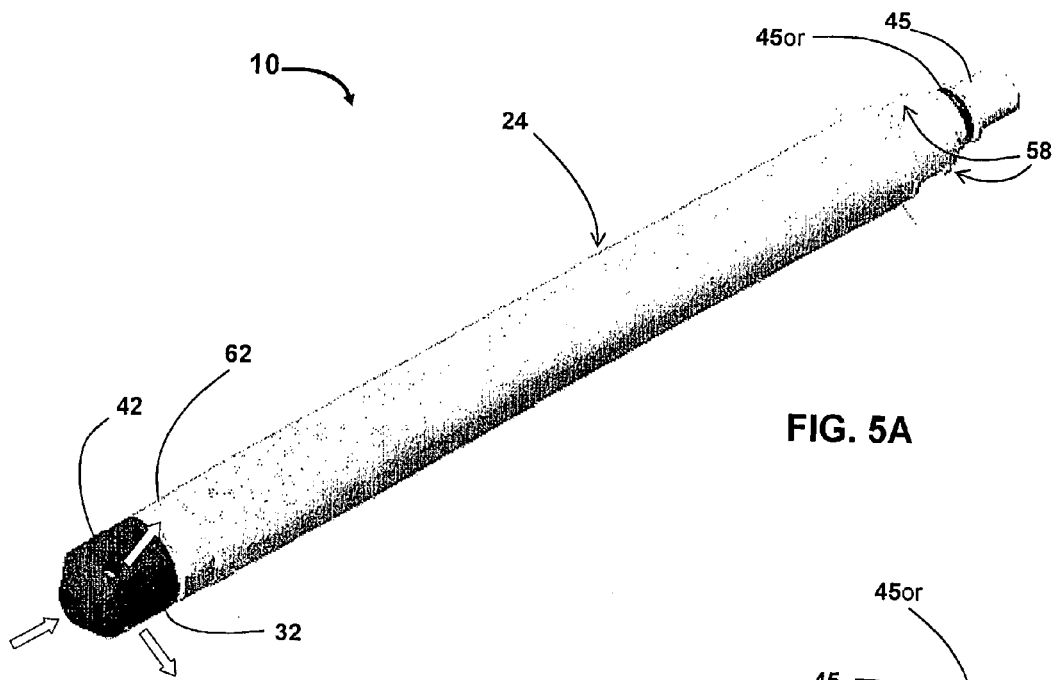
FIG. 5A is an isometric view of a probe assembly 10 of the invention.
Figure 5B:
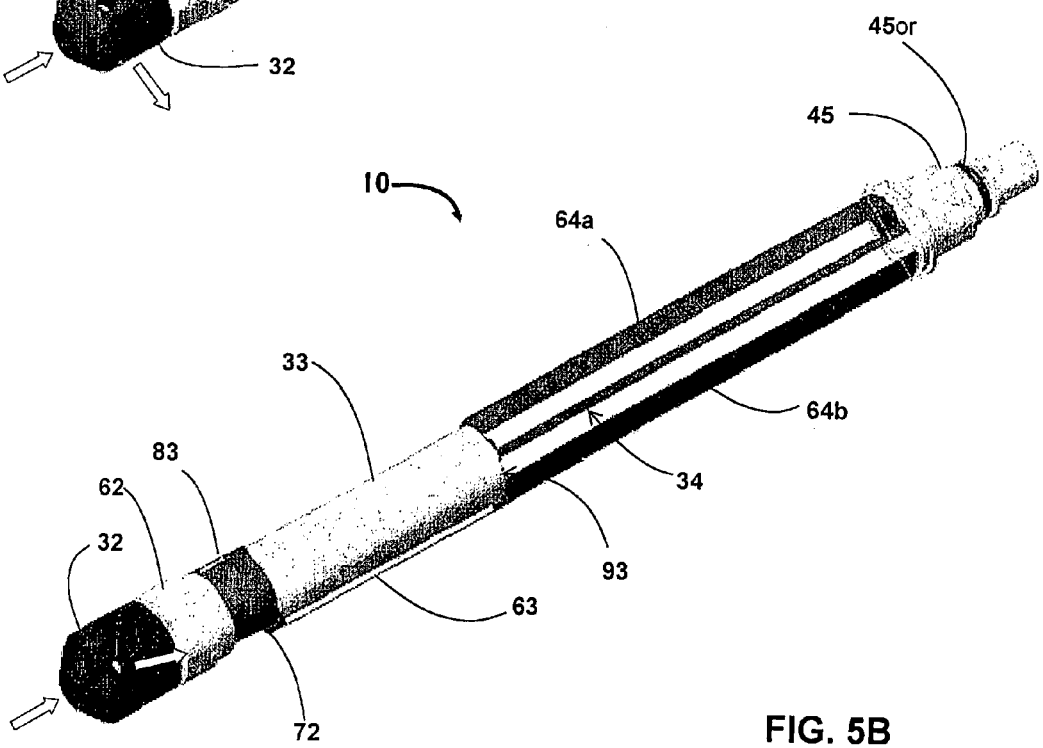
FIG. 5B is an isometric view, similar to that in FIG. 5A, whereby certain features of the probe 10 have been removed to show interior details.
Figure 5C:
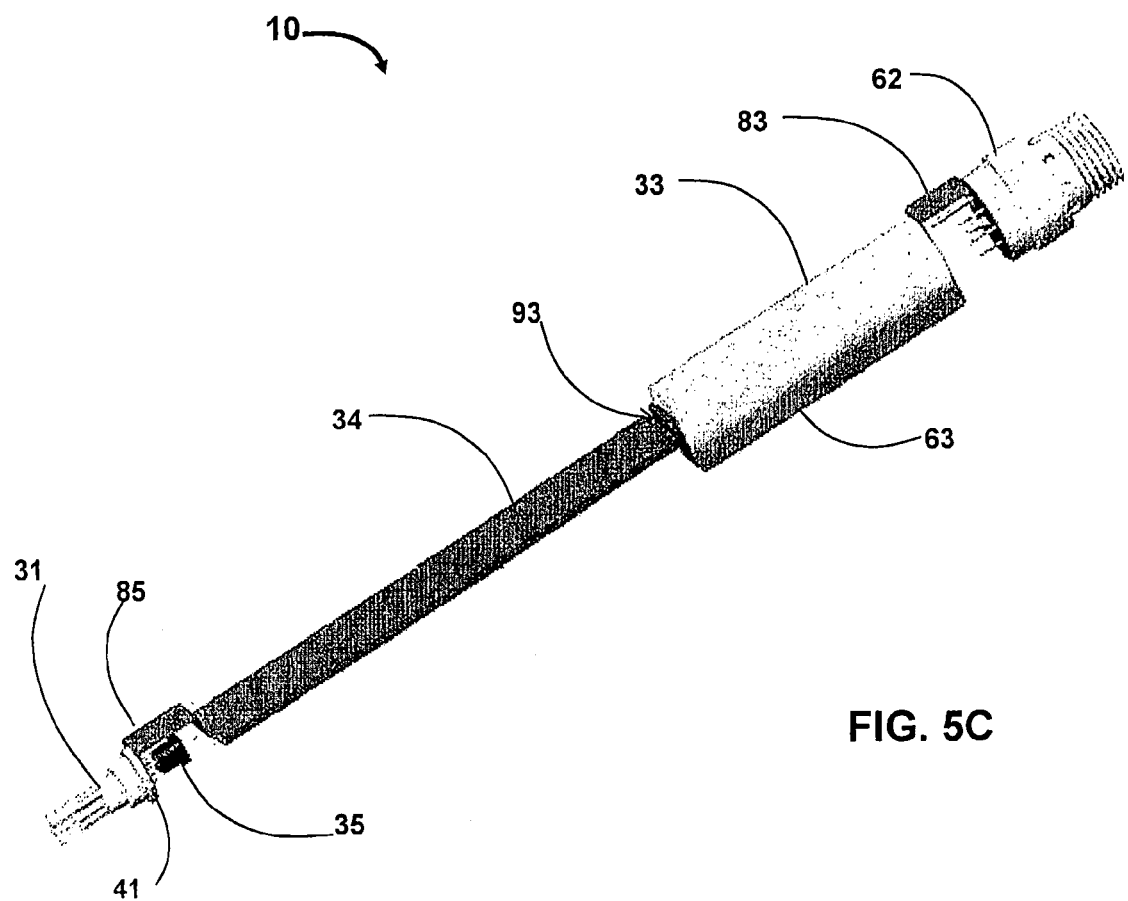
FIG. 5C is an isometric view, similar to that in FIG. 5B; certain additional features of the probe 10 have been removed to show further interior detail.
Figure 6A:
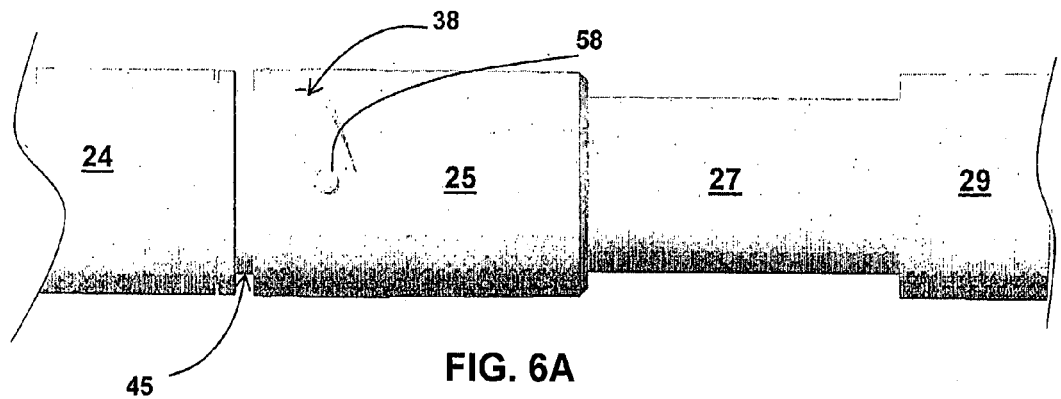
FIG. 6A is a side plan view of the probe section labeled 16 (FIGS. 2B, 3, 4A).
Figure 6B:
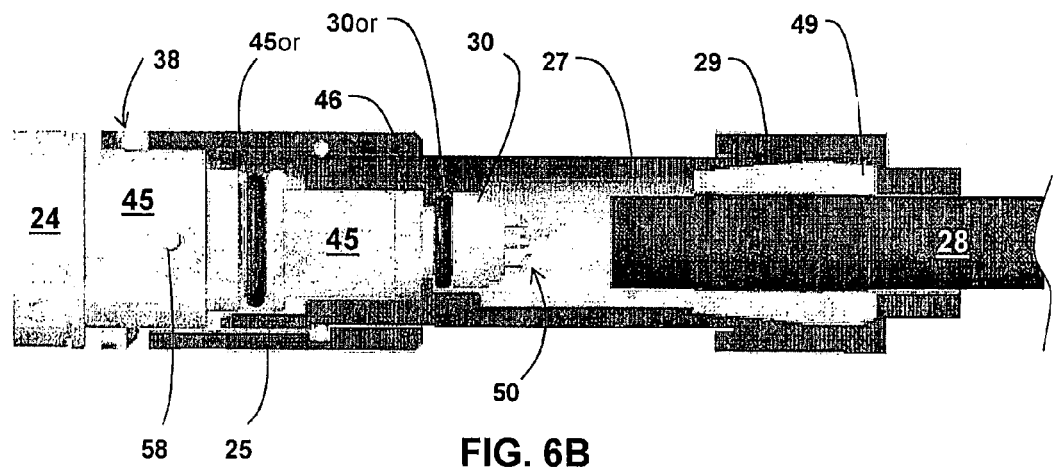
FIGS. 6B-6D are views of probe section 16 whereby certain features have been removed and/or depicted in cross-section fashion so as to detail the novel cam-twist type interconnect mechanism and other interior features.
Figure 6C:
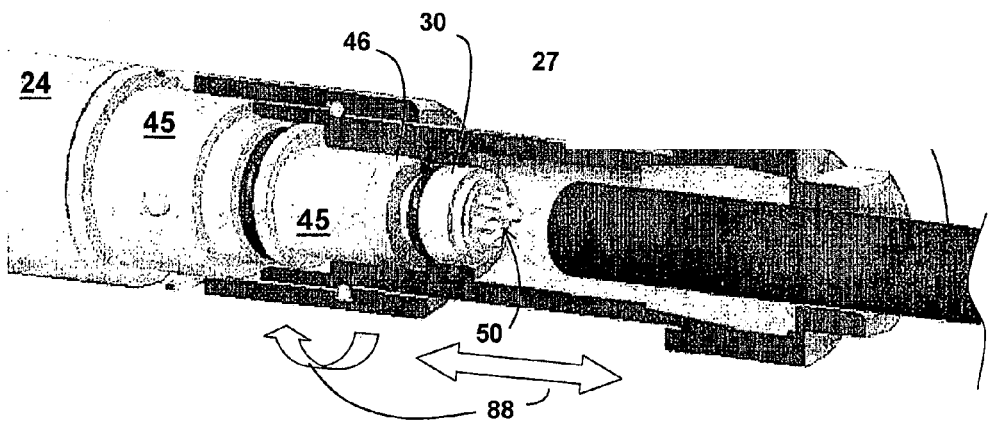
Figure 6D:
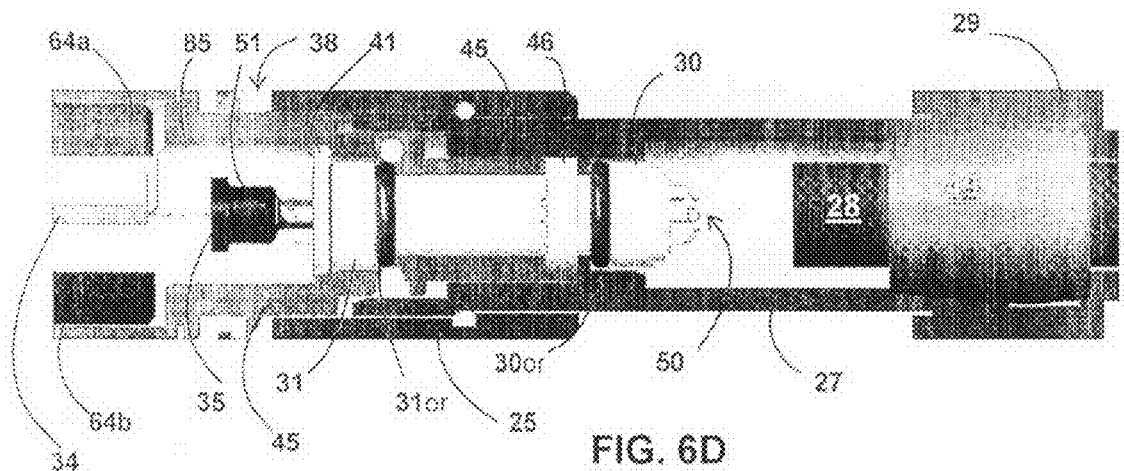
Figure 7A:
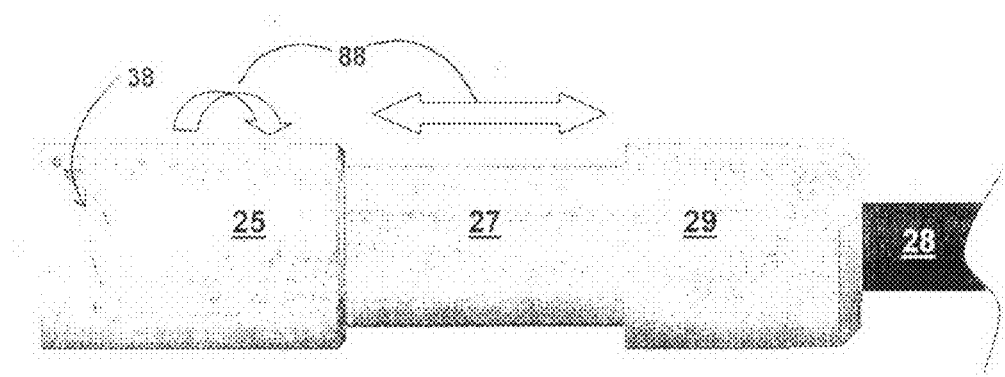
FIGS. 7A-7B are, respectively, side plan and isometric views of the unique interconnect features of a vented cable assembly of the invention—including female interconnect piece 27 along which a sleeve 25, having cammed apertures 38, slides.
Figure 7B:
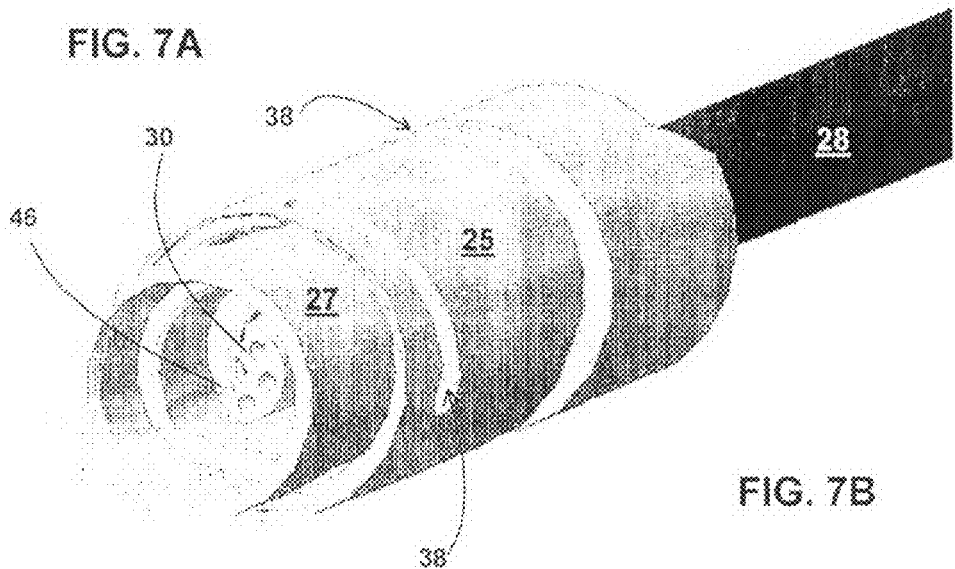
Figure 8A:
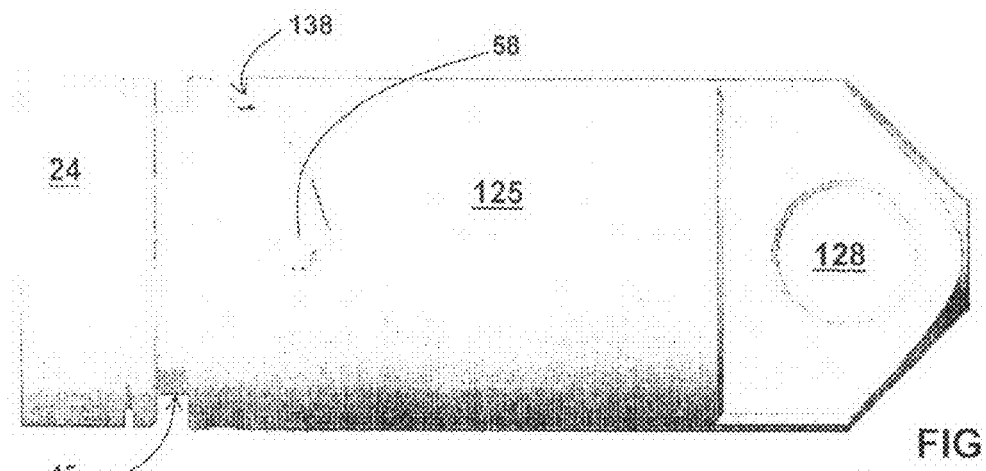
FIGS. 8A-8B are side plan views of the probe section 16 whereby, rather than connected vented cable assembly (FIGS. 7A-7B), a hanging backshell piece 125 is used having aperture 128 to which a cable (not shown) is connected for lowering the probe into a submersed position for monitoring.
Figure 8B:
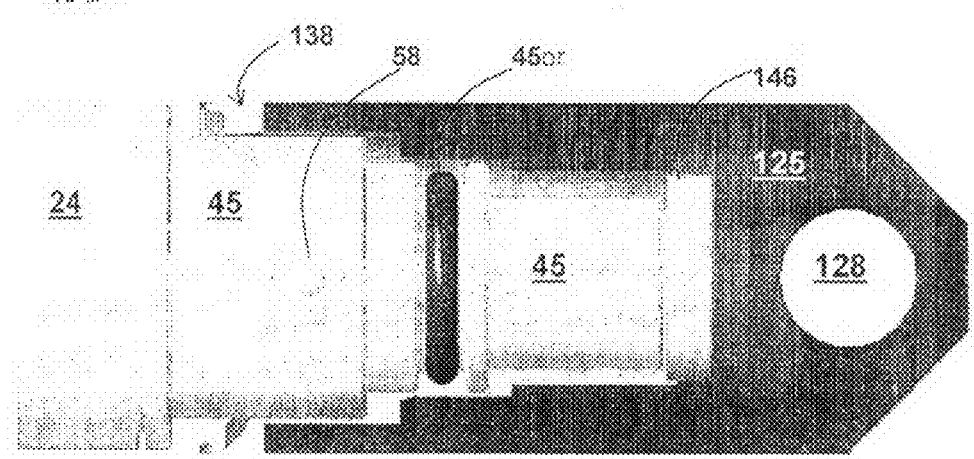
Figure 9:
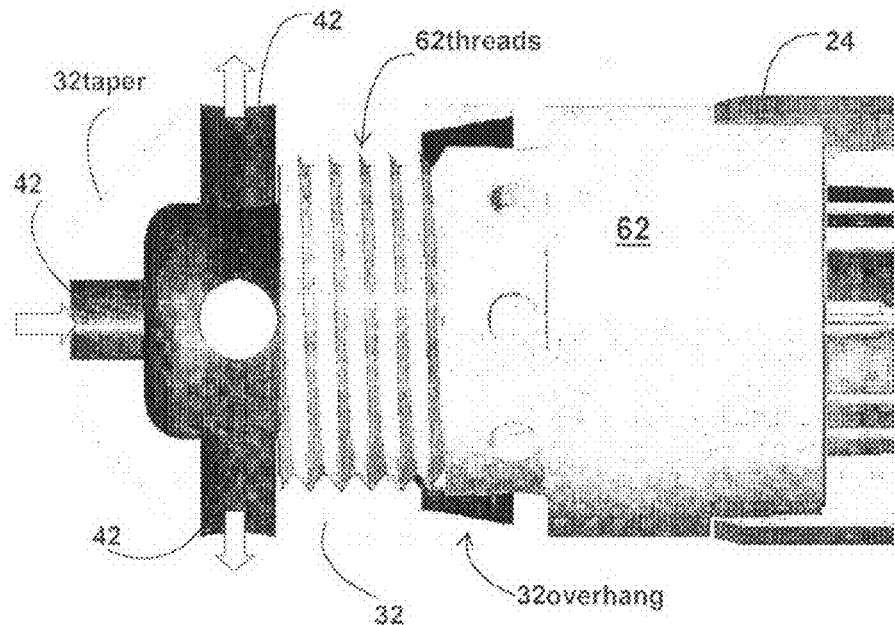
FIG. 9 is a side plan view of probe end labeled 12 (FIGS. 2B, 3, 4A); certain features have been removed and/or depicted in cross-section to view interior detail.

FIG. 4A is a side plan view of an assembled probe apparatus 10 whereby certain features of probe sections labeled 12, 16, 18 have been removed and/or depicted in cross-section fashion to show interior details. FIG. 4B is a side plan view of the assembled probe apparatus 10 of FIG. 4A whereby certain features of probe main-body section 14 have been removed and/or depicted in cross-section fashion to show interior details. FIG. 5A is another isometric view of a probe assembly 10. FIG. 5B is an isometric view, similar to that in FIG. 5A, whereby certain features of the probe 10 have been removed to show interior details. FIG. 5C is an isometric view, similar to that in FIG. 5B, whereby certain additional features of the probe 10 have been removed to show further interior detail. FIG. 6A is a side plan view of the probe section labeled 16 (FIGS. 2B, 3, 4A). FIGS. 6B-6D are views of probe section 16 whereby certain features have been removed and/or depicted in cross-section fashion so as to detail the novel cam-twist type interconnect mechanism and other interior features. FIGS. 7A-7B are, respectively, side plan and isometric views of the unique interconnect features of a vented cable assembly of the invention—including female interconnect piece 27 along which a sleeve 25, having cammed apertures 38, slides. FIGS. 8A-8B are side plan views of the probe section 16 whereby, rather than connected vented cable assembly (FIGS. 7A-7B), a hanging backshell piece 125 is used having aperture 128 to which a cable (not shown) is connected for lowering the probe into a submersed position for monitoring. FIG. 9 is a side plan view of probe end labeled 12 (FIGS. 2B, 3, 4A); certain features have been removed and/or depicted in cross-section fashion for viewing interior detail.

Figure 10A:
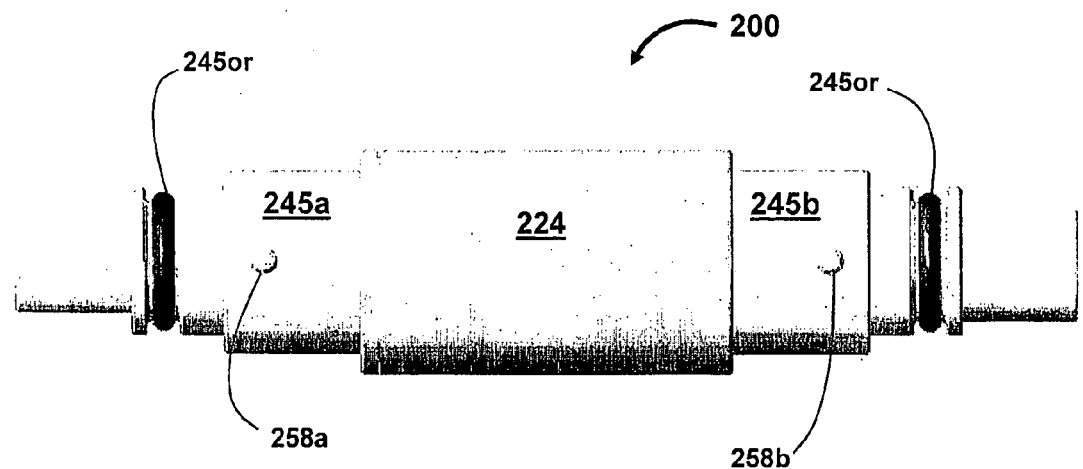
FIGS. 10A-10B are, respectively, side plan and isometric views of an extender assembly 200 comprising unique interconnect features—including male interconnect pieces 245a,b having respective protuberances 258a,b for operational association with female interconnects such as those shown on vented cable assembly (FIGS. 6A-D, 7A-B) and the backshell piece (FIGS. 8A-B).
Figure 10B:
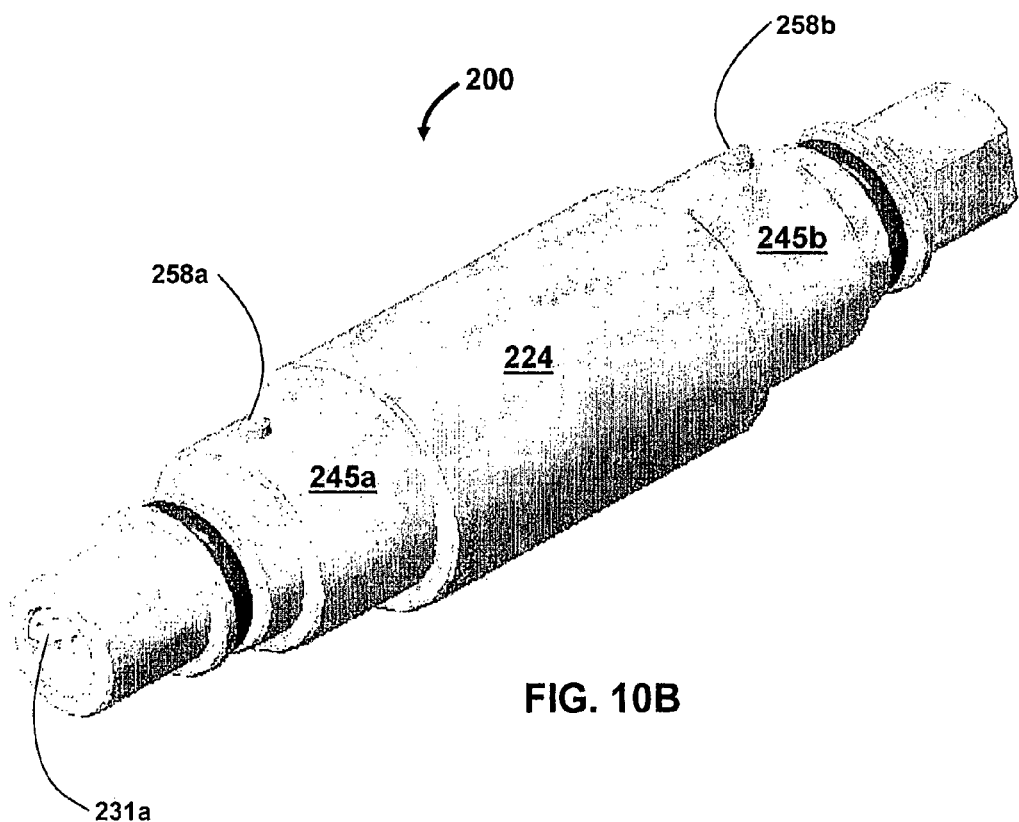
Figure 10C:
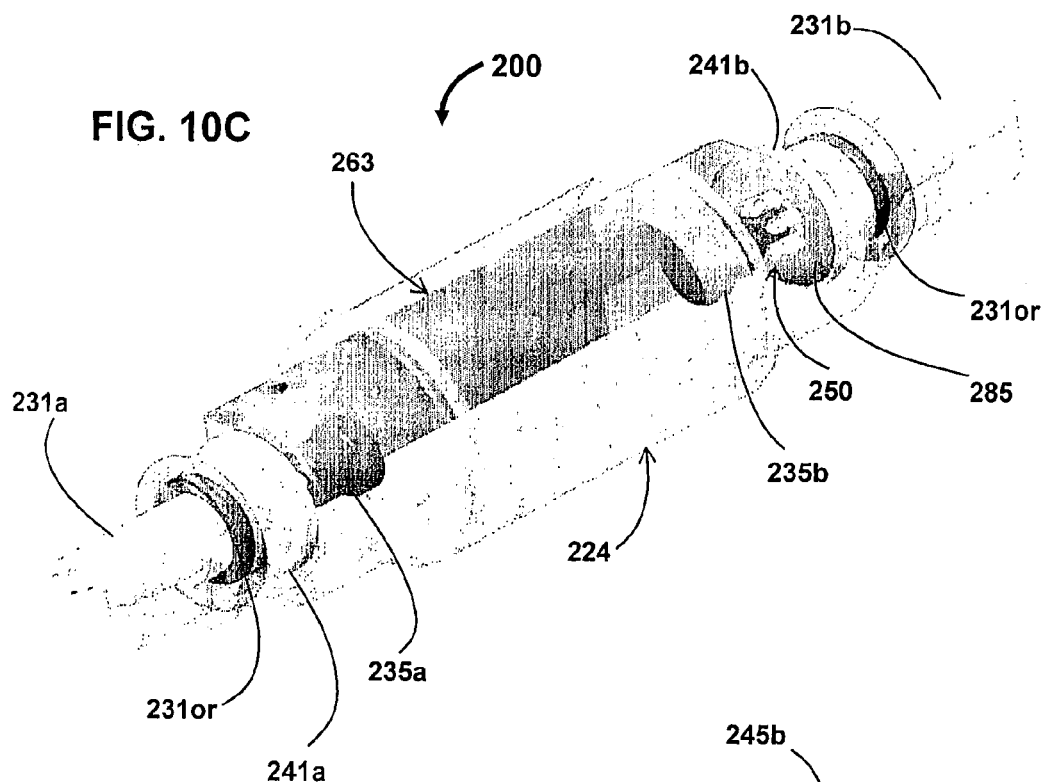
FIGS. 10C-10D are isometric views of extender assembly 200 of FIGS. 10A-10B whereby certain features have been removed and others depicted in exploded-assembly fashion, or in phantom, to view interior detail.
Figure 10D:
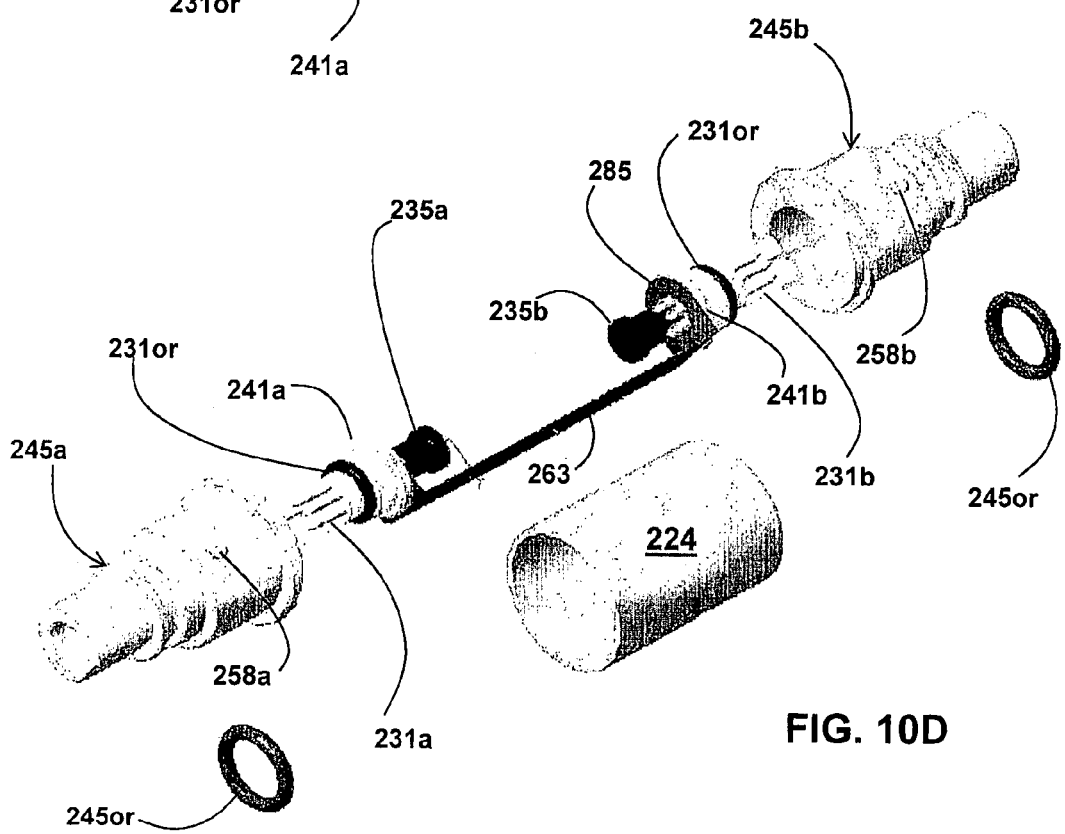
Figure 11A:
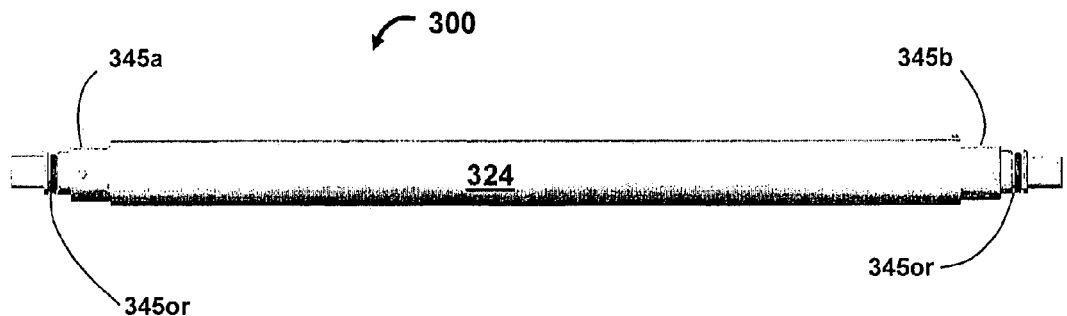
FIGS. 11A-11B are, respectively, side plan and isometric views of an alternative extender assembly 300 comprising unique interconnect features—including male interconnect pieces 345a,b having respective protuberances 358a,b for operational association with female interconnects such as those shown on vented cable assembly (FIGS. 6A-D and 7A-B) and the backshell piece (FIGS. 8A-B).
Figure 11B:
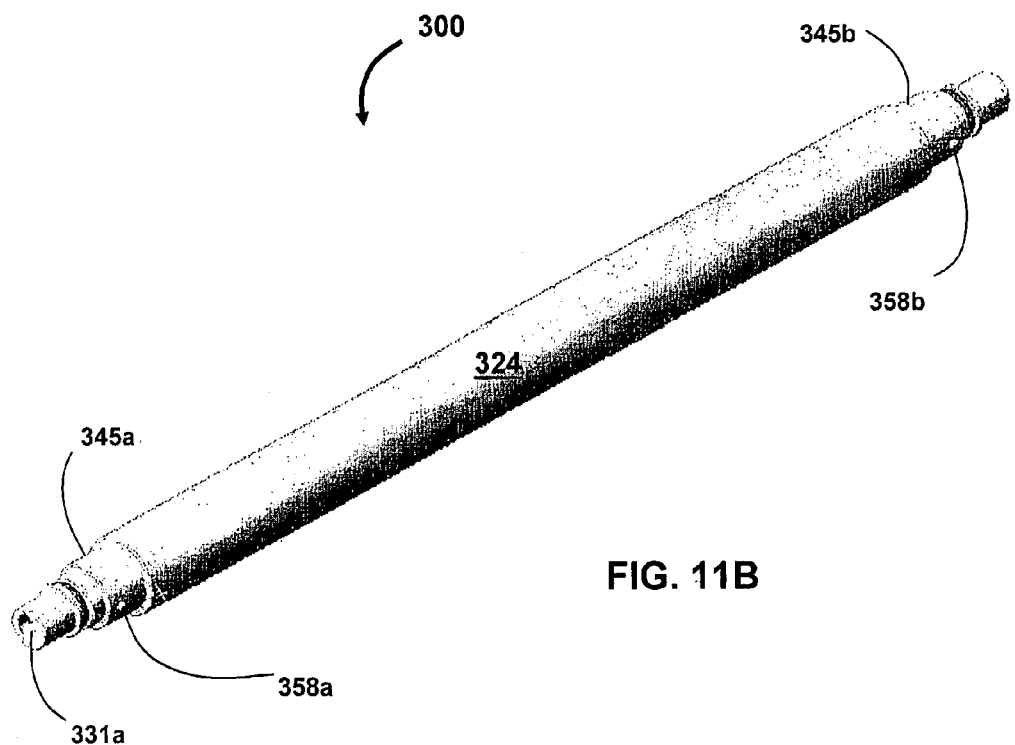
Figure 11C:
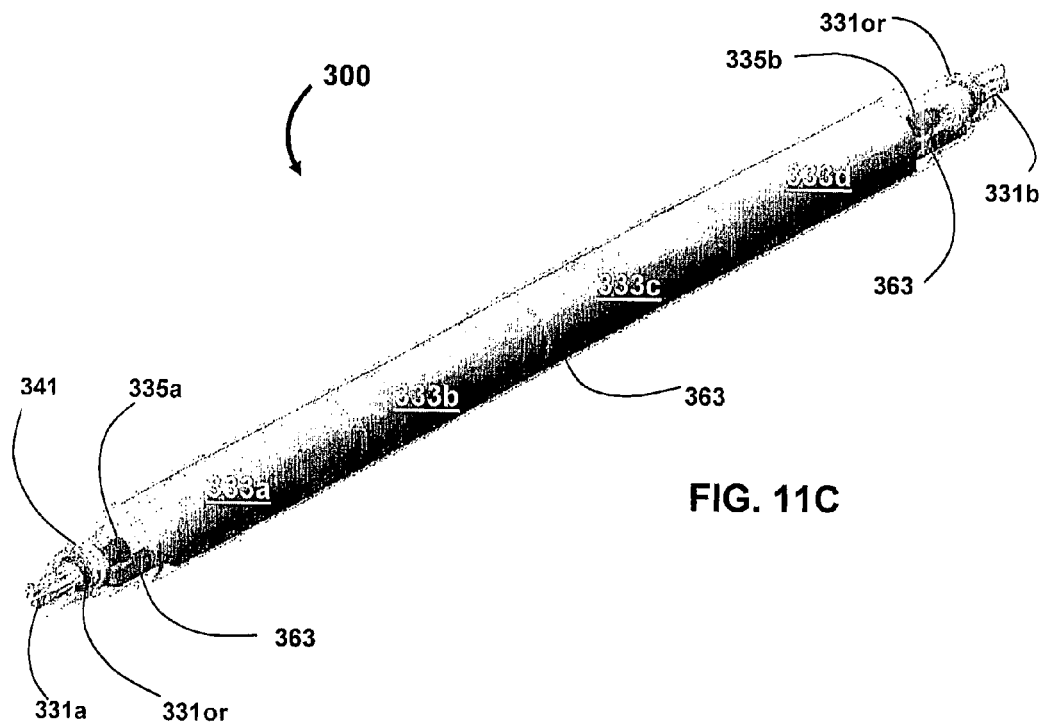
FIGS. 11C-11D are isometric views of extender assembly 300 of FIGS. 11A-11B whereby certain features have been removed and others depicted in exploded-assembly fashion, or in phantom, to view interior detail.
Figure 11D:
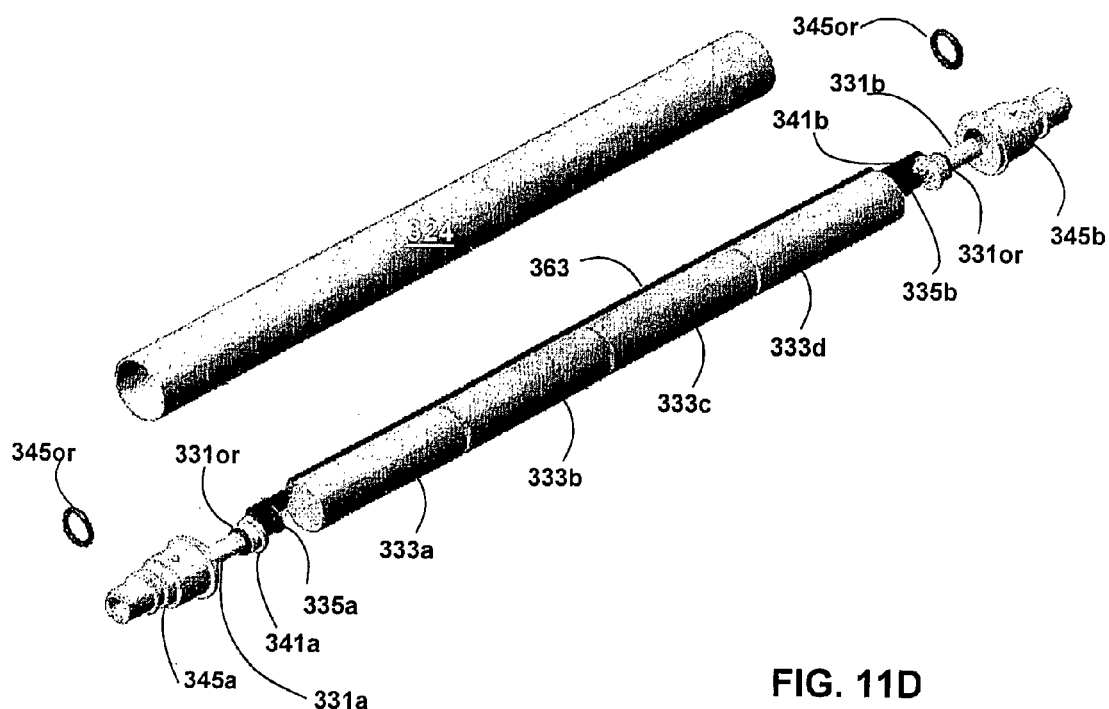
Figure 12A:
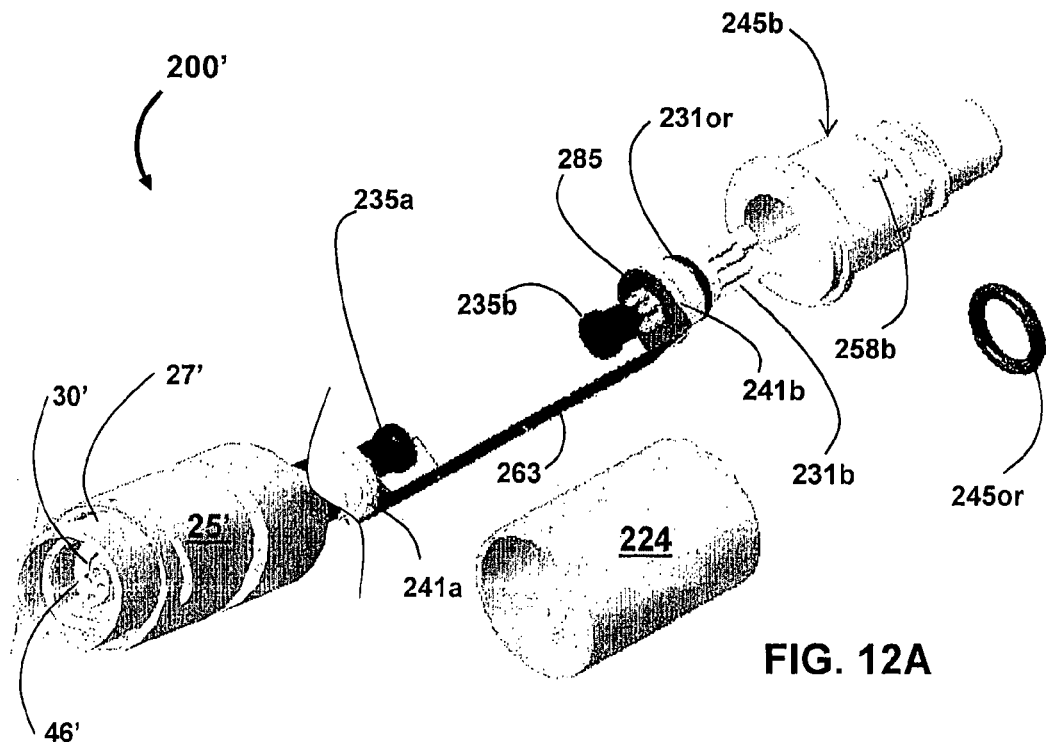
FIG. 12A is an isometric view of extender assembly 200' that shares several features of extender assembly 200 (FIG. 10D) except that a female interconnect piece 27' and associated sleeve 25' (see, also, FIG. 7B) are incorporated at one end; once again certain features have been removed and others depicted in exploded-assembly fashion, or in phantom, to view interior detail.
Figure 12B:
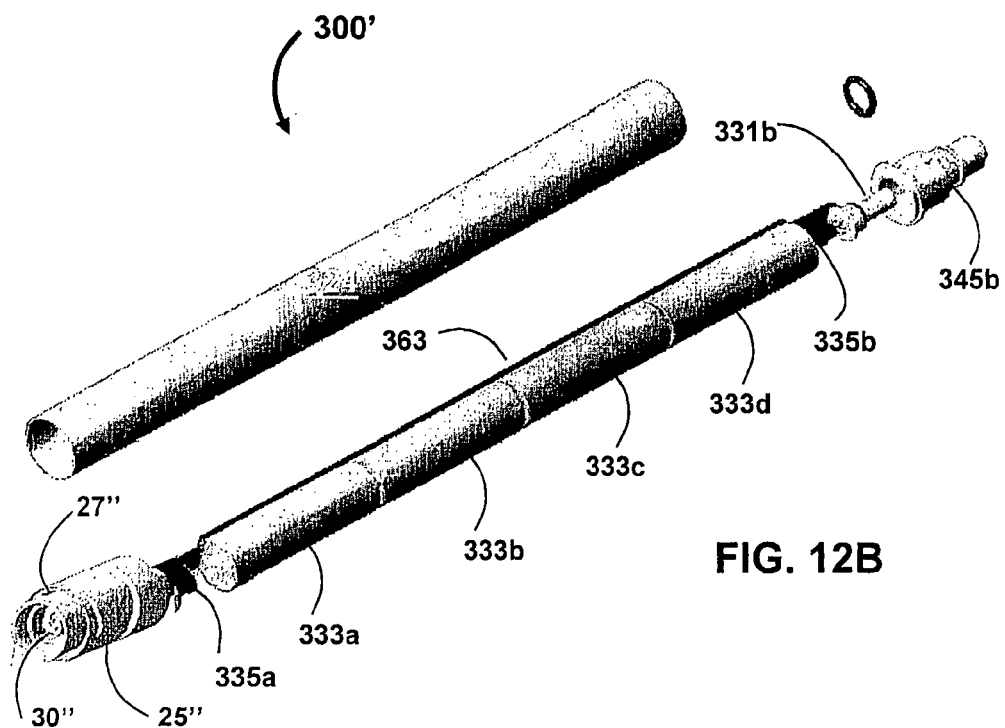
FIG. 12B is an isometric view of extender assembly 300' that shares several features of extender assembly 300 (FIG. 11D) except that a female interconnect piece 27" and associated sleeve 25" (see, also, FIG. 7B) are incorporated at one end; once again certain features have been removed and others depicted in exploded-assembly fashion, or in phantom, to view interior detail.

FIGS. 10A-10B are side plan and isometric views of an extender assembly 200, likewise FIGS. 11A-11B are views of an alternative extender assembly 300, comprising unique interconnect features for operational association with female interconnects such as those shown on vented cable assembly (FIGS. 6A-D and 7A-B) and the backshell piece (FIGS. 8A-B). FIGS. 10C-10D are isometric views of extender assembly 200, and likewise FIGS. 11C-11D are isometric views of alternative extender assembly 300, whereby certain features have been removed and others depicted in exploded-assembly fashion, or in phantom, to view interior detail. FIG. 12A is an isometric view of extender assembly 200' having several features similar to those of extender assembly 200 (FIG. 10D). Likewise FIG. 12B is an isometric view of extender assembly 300' having several features similar to those of extender assembly 300 (FIG. 11D). In both FIGS. 12A, 12B, certain features have been removed and others depicted in an exploded-assembly fashion or in phantom, permitting a view of the interior detail.

Returning to FIGS. 2B, 3, 4A-4B, etc.: probe apparatus 10 has features shown and labeled with reference numbers throughout the figures: Probe-body section 14 is shown having an outer tube 24 that houses a power source (electrochemical cell/battery 33) in communication with a printed circuit board assembly having an interior flexible wiring layer extending from either end of an elongated multi-layer circuit board 34 disposed between elongated weights 64a, 64b. Cone shaped end-cap 32 is connected to the sensing end 12 of probe-body 14. A new cam-twist type interconnect mechanism (section labeled 16, details best viewed in FIGS. 2B, 2D, 3, 4A-4B, 6B-D) includes several unique features: a male interconnect piece 45 secured to an end of the probe-body, the male interconnect piece 45 has at least one protuberance 58 outwardly-directed from an outer cylindrical surface; a female interconnect piece 27 has a cylindrical-section along which a sleeve 25 slides. Sleeve 25 of female interconnect piece 27 has at least one inclined aperture 38. If two inclined apertures 38 are included in sleeve 25—as seen better in FIGS. 7A-7B—the two included apertures 38 can be machined rotationally offset and generally parallel to each other. The inclined apertures 38 have inner surfaces that operate as cam surfaces adapted to accept a respective protuberance 58 of piece 45 (see, especially, FIGS. 6A and 8A) guiding the sleeve 25 into place as it is twisted. Arrows 88 in FIGS. 6C and 7A illustrate direction of slidable-movement of sleeve 25 over the outer smooth surface of female interconnect 27: Sleeve 25 can slide rotationally and longitudinally along the axis of female interconnect piece 27. Preferably, sleeve 25 slides longitudinally along cylindrical surface of interconnect piece 27 until each protuberance 58 is located within a respective bulbous end of an inclined aperture 38; as the sleeve is twisted into locking engagement against interconnect piece 45, the protuberance 58 slides along an inner cam surface of a respective inclined aperture 38 (enlarged details in FIGS. 6B-6D) into a second of the bulbous ends of the respective inclined aperture. A conductive spacer 41 (made of suitable metal, metal alloy, conductive polymer resin, etc.) is utilized for electrical connection with an extension of the flexible wiring layer/ribbon cable 85 (enlarged details in FIGS. 5C, 6D, and 3). Selectively located O-rings labeled 45 or, 30 or, and 31 or (see FIGS. 6B-6D and elsewhere) provide further positional stability for components of the cam-twist type interconnect mechanism 16.

Shown more-particularly in FIGS. 3, 4B, 5C, 6D: A barrier assembly is housed within the male interconnect 45 and shown disposed between an end of the elongated multi-layer circuit board 34 and conductive spacer 41; as mentioned the barrier assembly has a membrane, such as that within off-the-shelf component 36 known as a 'hydrophobic vent' which is distributed/manufactured by a company called Promepla located outside of the U.S. Preferably the hydrophobic vent component 36 has a membrane made of a material that is generally liquid impermeable yet gas permeable—permitting air pressure to equalize within the probe-body compartment 14 with that outside, above-ground so that a difference can be logged on-board the probe 10. The barrier assembly also has a collar 35 shaped for securing the membrane component 36 in position within the cam-twist type interconnect mechanism. Note that the extension of the flexible wiring layer/ribbon cable labeled 85 has been redirected around the barrier assembly 35/36 (enlarged details in FIGS. 5C, 6D, and 3).

As detailed in FIGS. 3, 6B-6D: A toriod-shaped mechanical seal 46 preferably made of a non-metallic material such as silicon, Santoprene, and so on, is disposed around a keyed-connector 30 (for example, as shown and mentioned above, suitable connectors include LEMO® brand electrical keyed-type connectors) is housed within the female interconnect piece 27. Preferably, the multi-layer circuit board 34 comprises processor circuitry for carrying out data logging functionality using information collected about the aqueous environment. Note that throughout various of the figures, an end of the female interconnect piece 27 is secured to a vented cable assembly having vented cabling 28, uniquely shaped collar 29, and internal spacer 49.

Turning to FIGS. 2E-2F and 9, further details of the end-cap 32 can be appreciated; also shown is an electrical connector piece 62 keyed for positioning to the end of the probe-body 14. Multiple openings 42 within end-cap 32 permit water (or other fluid within which the end section 12 has been submersed for monitoring) to pass. A taper $32_{taper}$ at the 'nose' of end-cap gives it a cone shape; and an overhang $32_{overhang}$ partially covers several apertures located around the circumference of the connector piece 62 to aid in keeping debris within the aqueous environment being monitored from entering/clogging apertures of 62. Although not shown for simplicity, the end-cap 32 houses at least one liquid parameter sensing unit such as an off-the-shelf pressure and/or temp. sensor (by way of example, GE Druck out of Leicester, United Kingdom manufactures a suitable pressure sensor), permitting data concerning water pressure and/or temperature to be collected at the end section 12.

FIGS. 8A-8B illustrate a unique 'hanging backshell' design that incorporates the novel cam-twist type interconnect mechanism featuring: a male interconnect piece 45 secured to an end of probe-body 14 in a manner as depicted and described elsewhere (e.g., FIGS. 2B, 3, 4A); the male interconnect piece 45 having at least one protuberance 58 outwardly-directed from an outer cylindrical surface; a female interconnect piece 125 that has an enclosed-end with an aperture 128 (to which a hook or other mechanism/cabling may be fastened); and at least one, and preferably two, inclined apertures 138 for accepting a respective protuberance 58, in a manner as described above. Note that other unique features housed by, and/or utilized in connection with, the unique male interconnect 45 (see FIGS. 6B-6D, etc. for reference)—such as conductive spacer 41 used to provide a means by which electrical connection can be made with an extension 85 of flexible wiring, the generally liquid impermeable barrier assembly 35/36, etc.—are preferably also incorporated with a probe assembly comprising the new hanging backshell. This permits interchangeability between connecting female interconnect piece 27 secured to a vented cable assembly (28, 49. 29, etc.) or 'hanging backshell' female interconnect piece 125—both of which have been uniquely designed and suitable for fabrication out of metal using known metal fab techniques (machining, cutting, stamping, etc.) with tolerances sufficient to maintain the fluid-tight probe-body compartment that houses on-board probe circuitry (e.g., such as the multi-layer circuit board 34, flexible ribbon-wiring extensions therefrom 63/83 and 85, along with electrical connectors) and associated on-board power source (e.g., extended life battery/electrochemical cell 33).

The unique design of the novel cam-twist type interconnect mechanism eliminates the requirement for epoxy/chemical adhesion means by utilizing certain novel, cooperating features: a press fit toroid-shaped mechanical seal (at 46 in FIG. 3, et al., and close-up in FIGS. 6B-D) made of Silicon, Santoprene, or other suitable polymeric material; o-rings have been placed as labeled 300 or, 31 or, 45 or in FIGS. 3, 4A, 6B, 6D; a secure fit between the uniquely shaped male interconnect piece 45 and female interconnect piece 27 along which a sleeve 25, having cammed apertures 38, slides; as well as a metal spacer (at 41 in FIG. 3, et al., close-up in FIG. 6D) to which a portion of ribbon cable (labeled at 85 in FIGS. 5C and 6D) is welded.

Turning next to FIGS. 10A-D and 11A-D, extender assemblies 200, 300 each have unique interconnect features—including male interconnect pieces 245a,b and 345a,b having respective protuberances 258a,b and 358a,b for operational association with female interconnects, such as those shown on vented cable assembly (FIGS. 6A-D and 7A-B) and the backshell piece (FIGS. 8A-B), in a manner similar to that of uniquely shaped male interconnect piece 45 with female interconnect piece 27 plus sleeve 25, or hanging backshell female interconnect piece 125 (FIGS. 8A-B). A body section comprising an outer tube (224 in FIGS. 10A-D and 324 in FIGS. 11A-D) is disposed between respective male interconnect pieces 245a,b and 345a,b to house a variety of internal features of an extender assembly 200, 300.

A barrier assembly is housed within each male interconnect 245a, 245b, 345a, 345b and, as shown, preferably disposed between a central portion of the assembly and a respective conductive spacer 241a, 241b, 341a, 341b. The barrier assembly has a membrane, such as that within a 'hydrophobic vent' (an off-the-shelf component, see FIG. 3 at 36 and associated discussion herein), and a respective collar 235a, 235b, 335a, 335b shaped for securing the membrane component 36 in position within the cam-twist type interconnect mechanism. As mentioned elsewhere herein, preferably the hydrophobic vent component 36 has a membrane made of a material that is generally liquid impermeable yet gas permeable. The respective conductive spacer 241a, 241b, 341a, 341b (made of suitable metal, metal alloy, conductive polymer resin, etc.) is utilized for electrical connection with an internal flexible wiring layer/ribbon cable 263, 363 extending along the inside of tubular housing 224, 324. Note that the flexible wiring layer/ribbon cable labeled 263, 363 has been redirected around the barrier assemblies (enlarged details in FIGS. 3, 5C, 6D at 35/36, for example). As depicted in FIGS. 11C-11D, flexible wiring layer/ribbon cable 363 is redirected around several battery cells 333a-d. The FIGS. 11A-D extender assembly embodiment may be employed as additional, or backup, power source for the probe apparatus handily retrofit to an apparatus already in place performing monitoring functions. Battery cells 333a-d may be any suitable electrochemical cells sized to fit within housing 324, which although shown as tubular, may have a cross section of any suitable shape (oval, hexagonal, square, and so on). Likewise, although outer housing 24, 224 are depicted as tubular in shape, these, too may be of a variety of suitable shapes (oval, hexagonal, square, and so on). Selectively located O-rings labeled 245 or and 345 or (around interconnect pieces 245a,b and 345a,b) and 231 or and 331 or (around electrical connectors 231a,b and 331a,b) provide further positional stability for components of the cam-twist type interconnect mechanism utilized at each end portion of respective extender assemblies 200, 300.

In operation within the context of the extender assemblies 200, 300 (FIGS. 10A-D and 11A-D), the new cam-twist type interconnect mechanism is employed in a manner similar to that depicted by FIGS. 6A-D and 7A-B, as follows: inclined apertures 38 of a sleeve member/piece (e.g., 25 or 125) have inner surfaces that operate as cam surfaces adapted to accept a protuberances 258a, 258b, 358a, 358b of a respective piece 245a, 245b, 345a, 345b guiding the sleeve 25 (or piece 125) into place as it is twisted. For example, arrows 88 in FIGS. 6C and 7A illustrate direction of slidable-movement of sleeve 25 over the outer smooth surface of female interconnect 27: Preferably, sleeve 25 slides along cylindrical surface of interconnect piece 27 until each protuberance of a male interconnect 245a, 245b, 345a, 345b is located within a respective bulbous end of an inclined aperture 38; as the sleeve is twisted into locking engagement against an interconnect piece (245a, 245b, 345a, 345b), the protuberance (258a, 258b, 358a, 358b) slides along an inner cam surface of a respective inclined aperture 38 (enlarged details in FIGS. 6B-6D) into a second of the bulbous ends of the respective inclined aperture. As the interconnect mechanism pieces lock into place, an electrical connector 231a, 231b, 331a, 331b (for example, as mentioned, suitable connectors include LEMO® brand electrical keyed-type connectors) within the male interconnect is gently keyed into position for electrical communication with a respectively keyed-electrical connector (e.g., at 30) of female interconnect piece (e.g., 27) so that information may, e.g., be transmitted along vented cable assembly.

Turning to alternate extender assemblies 200' and 300' of FIGS. 12A-B, which respectively share several features of extender assemblies 200 and 300 of FIGS. 10D, 11D, a female interconnect piece at 25'/27' and 25"/27" may be employed at an end of the extender assembly such that the extender assembly 200', 300' may be interconnectable with respective male interconnect piece(s) such as those labeled 45 of probe apparatus 10 or 245a/b, 345a/b of extender assemblies configured as shown at 200, 300, 200', and 300' creating component configurations such as those at 100A-100C in FIGS. 13A-C. Core features of female interconnect piece(s) at 25'/27' and 25"/27" operate in a manner similar to female interconnect piece(s) at 25/27 as described throughout.

The alternate configurations of combinations of the novel elements described herein are schematically depicted in FIGS. 13A-C. These schematics further identify preferred positioning of novel features of a barrier assembly (235/36a, 235/36b, 335/36a, 335/36b) along with the twist-type interconnect mechanisms, each of which preferably comprise novel features of individual interconnect pieces (male and female) as described herein, using like reference numerals of other figures. FIG. 13A depicts a couple of extender assemblies (distinguished as "A" and "B" for reference, only) disposed between probe apparatus 10 and a cable assembly female interconnect 25/37 to which a vented cable (as discussed above) is connected for data transfer to a PDA (personal desk assistant) adapted, for accessing data storage. FIG. 13B depicts probe apparatus 10 connected with female interconnect piece 25/27 connected to a microprocessor & transmitter unit through a vented cable. FIG. 13C depicts an extender assembly "A" disposed between probe apparatus 10 and a hanging backshell/female interconnect piece 125/128, to which a support cable is threaded for holding the probe apparatus while submersed.

EXAMPLE 1

By way of example only in connection with embodiments of the probe apparatus structures shown and depicted here-throughout, in operation, the probe apparatus can be operated to perform monitoring of aqueous environment using capabilities and functionalities such as those described in the technical description from assignee-PCT applicant's mini-TROLL® OPERATOR'S MANUAL rev. 006 10/03.

As one will appreciate, the probe apparatus designed is readily manufacturable as well as handy to assemble/exchange various probe body embodiments with different vented cable assemblies and hanging backshell designs. The unique probe design features: a long-life battery, titanium probe-body housing and associated outer components, as well as new internal 'hydrophobic vent' assembly that permits fluids in a gas state (e.g., air at atmospheric pressure) to enter the probe-body compartment where data collection/sensing, logging, processing, and storage takes place, while preventing fluids in a liquid state from entering and damaging exposed circuitry, wiring, and battery cells therewithin. The flexible elongated circuit board and novel ribbon cabling permits ready adaptation of the probe to incorporate additional functional features by programming the circuitry 'on-board' the probe or one or more externally/remotely located desktop or portable processing units used to download information collected and transmitted from the probe body.

The novel extender assembly design permits handy retrofit with probe apparatus components having mating cam-type interconnect mechanism capability providing either length extension to a probe assembly (wherein other features or electrical components may be housed to provide additional functionalities for the probe) or additional, or backup, power source located in a submersible package—both of which may be purchased separately and taken 'on-site' after a probe apparatus is in place, monitoring.

While certain representative embodiments and details have been shown for the purpose of illustrating the invention, those skilled in the art will appreciate that various modifications, whether specifically or expressly identified herein, may be made to these representative embodiments without departing from the novel core teachings or scope of this technical disclosure. Accordingly, all such modifications are intended to be included within the scope of the claims. Furthermore, in any claim that is filed herewith or hereafter, any means-plus-function clauses used, or later found to be present, are intended to cover at least all structure(s) described herein as performing the recited function and not only structural equivalents but also equivalent structures.

We claim:

1. A submersible probe apparatus for monitoring parameters within an aqueous environment, the apparatus comprising:
    (a) a probe-body comprising an outer tube housing a power source in communication with a printed circuit board assembly having an interior flexible wiring layer extending from either end of an elongated multi-layer circuit board disposed between a first and second elongated weight;
    (b) an end-cap for connecting with a first end of the probe-body; and
    (c) a cam-twist type interconnect mechanism comprising:
        a male interconnect piece secured to a second end of the probe-body,
        the male interconnect piece having at least one protuberance outwardly-directed from an outer cylindrical surface,
        a female interconnect piece having a cylindrical-section along which a sleeve having at least one inclined aperture, may slide, and the inclined aperture is adapted for accepting the protuberance.

2. The probe apparatus of claim 1 further comprising a conductive spacer with which a second extension of the flexible wiring layer is in electrical communication, and a barrier assembly housed within the male interconnect piece and disposed between a second end of the elongated multi-layer circuit board and the conductive spacer; the barrier assembly comprising a membrane generally liquid impermeable and gas permeable.

3. The probe apparatus of claim 2 wherein:(a) the barrier assembly further comprises a collar for securing the membrane in position within the cam-twist type interconnect mechanism;(b) a toroid-shaped mechanical seal disposed around a keyed-connector is housed within the female interconnect piece; and(c) the multi-layer circuit board comprises processor circuitry for carrying out data logging functionality using information collected about the aqueous environment.

4. The probe apparatus of claim 2 wherein an end of the female interconnect piece is secured to a vented cable assembly.

5. The probe apparatus of claim 1 wherein:
(a) the end-cap houses at least one liquid parameter sensing unit
(b) the first end of the probe-body comprises an electrical connector keyed for positioning to a keyed-connector housed within the female interconnect piece; and
(c) a second extension of the flexible wiring layer is welded to a conductive spacer.

6. An extender assembly for operational association with the probe apparatus of claim 1, the extender assembly comprising:
(a) a second male interconnect piece located at an end of the extender assembly for operational association with the female interconnect piece, the second male interconnect piece comprising at least one protuberance outwardly-directed from a second outer cylindrical surface; and
(b) an extender assembly housing within which a second flexible wiring layer extends, the flexible wiring layer in electrical communication with an electrical connector keyed for positioning with a keyed-connector housed within the female interconnect piece.

7. The extender assembly of claim 6 further comprising a third male interconnect piece located at a second end of the extender assembly, the third male interconnect piece comprising at least one protuberance outwardly-directed from a third outer cylindrical surface; and wherein the second flexible wiring layer is in electrical communication with a second electrical connector.

8. The extender assembly of claim 6 further comprising a plurality of electrochemical cells within the extender assembly housing and positioned along the second flexible wiring layer.

9. An extender assembly for operational association with a submersible probe apparatus for monitoring parameters within an aqueous environment:
(a) the probe apparatus comprising a probe-body comprising an outer tube and first and second ends; and a cam-twist type interconnect mechanism comprising a male interconnect piece secured to the second end and a female interconnect piece; and
(b) the extender assembly comprising a housing within which a flexible wiring layer extends, the flexible wiring layer in electrical communication with an electrical connector keyed for positioning with a keyed-connector housed within the female interconnect piece.

10. The extender assembly of claim 9 wherein:
the male interconnect piece has at least one protuberance outwardly-directed from an outer cylindrical surface,
the female interconnect piece has a cylindrical-section along which a sleeve having at least one inclined aperture, may slide, and
the inclined aperture is adapted for accepting the protuberance.

11. The extender assembly of claim 9 further comprising:
(a) a second male interconnect piece located at a first end of the extender assembly for operational association with the female interconnect piece, the second male interconnect piece comprising at least one protuberance outwardly-directed from a second outer cylindrical surface; and
(b) a second female interconnect piece located at a second end of the extender assembly, the second female interconnect piece having a second cylindrical-section along which a second sleeve having at least one inclined aperture, may slide.

12. A submersible probe apparatus for monitoring parameters within an aqueous environment, the apparatus comprising:
(a) a probe-body comprising an outer tube housing a power source in communication with a printed circuit board assembly having an interior flexible wiring layer extending from either end of an elongated multi-layer circuit board disposed between a first and second elongated weight;
(b) an end-cap for connecting with a first end of the probe-body; and
(c) a cam-twist type interconnect mechanism comprising:
a male interconnect piece secured to a second end of the probe-body,
the male interconnect piece having at least one protuberance outwardly-directed from an outer cylindrical surface,
a female interconnect piece having an enclosed-end and at least one inclined aperture adapted for accepting the protuberance.

13. The probe apparatus of claim 12 further comprising a conductive spacer with which a second extension of the flexible wiring layer is in electrical communication, and a barrier assembly housed within the male interconnect piece and disposed between a second end of the elongated multi-layer circuit board and the conductive spacer; the barrier assembly comprising a membrane generally liquid impermeable and gas permeable; and a toroid-shaped mechanical seal housed within the female interconnect piece.

14. The probe apparatus of claim 12 wherein:(a) the barrier assembly further comprises a collar for securing the membrane in position within the cam-twist type interconnect mechanism; and(b) an aperture at the enclosed-end of the female interconnect piece has a cable assembly hooked thereto for hanging the female interconnect from the cable assembly.

15. An extender assembly for operational association with the probe apparatus of claim 12, the extender assembly comprising:
(a) a second male interconnect piece located at an end of the extender assembly for operational association with the female interconnect piece, the second male interconnect piece comprising at least one protuberance outwardly-directed from a second outer cylindrical surface; and
(b) an extender assembly housing within which a second flexible a wiring layer extends, the flexible wiring layer in electrical communication with an electrical connector keyed for positioning with a keyed-connector housed within the female interconnect piece.

16. The extender assembly of claim 15 further comprising a third male interconnect piece located at a second end of the extender assembly, the third male interconnect piece comprising at least one protuberance outwardly-directed from a third outer cylindrical surface; and wherein the second flexible wiring layer is in electrical communication with a second electrical connector.

17. The extender assembly of claim 15 further comprising a second female interconnect piece located at a second end of the extender assembly, the second female interconnect piece having a second cylindrical-section along which a second sleeve having at least one inclined aperture, may slide, the inclined aperture is adapted for accepting a protuberance outwardly-directed from an outer cylindrical surface of a third male interconnect piece located at an end of a second extender assembly.

18. The extender assembly of claim 15 further comprising a plurality of electrochemical cells within the extender assembly housing and positioned along the second flexible wiring layer.

19. A submersible probe apparatus for monitoring parameters within an aqueous environment, the apparatus comprising:
  (a) a probe-body comprising an outer tube and a first end;
  (b) a cam-twist type interconnect mechanism comprising:
    a male interconnect piece secured to a second end of the probe-body,
    the male interconnect piece having at least one protuberance outwardly-directed from an outer cylindrical surface,
    a female interconnect piece having a cylindrical-section along which a sleeve having at least one inclined aperture, may slide, and
    the inclined aperture is adapted for accepting the protuberance; and
  (c) an extender assembly comprising a second male interconnect piece located at an end of the extender assembly for operational association with the female interconnect piece, the second male interconnect piece comprising at least one protuberance outwardly-directed from a second outer cylindrical surface.

20. The probe apparatus of claim 19 wherein:
  (a) the extender assembly further comprises a third male interconnect piece located at a second end of the extender assembly, the third male interconnect piece comprising at least one protuberance outwardly-directed from a third outer cylindrical surface; and
  (b) the outer tube of the probe-body houses a power source in communication with a printed circuit board assembly having an interior flexible wiring layer extending from either end of an elongated multi-layer circuit board disposed between a first and second elongated weight.

21. The probe apparatus of claim 20 wherein the extender assembly further comprises an extender assembly housing within which a second flexible wiring layer extends, the flexible wiring layer in electrical communication with an electrical connector keyed for positioning with a keyed-connector housed within the female interconnect piece.

22. An extender assembly operationally combined with a submersible probe apparatus for monitoring parameters within an aqueous environment:
  (a) the probe apparatus comprising a probe-body comprising an outer tube and first and second ends; and a cam-twist type interconnect mechanism comprising a male interconnect piece secured to the second end and a female interconnect piece;
  (b) the extender assembly comprising a housing within which a flexible wiring layer extends, the flexible wiring layer in electrical communication with an electrical connector keyed for positioning with a keyed-connector housed within the female interconnect piece;
  (c) the male interconnect piece has at least one protuberance outwardly-directed from an outer cylindrical surface;
  (d) the female interconnect piece has a cylindrical-section along which a sleeve having at least one inclined aperture, may slide; and
  (e) the inclined aperture is adapted for accepting the protuberance.

23. An extender assembly operationally combined with a submersible probe apparatus for monitoring parameters within an aqueous environment:
  (a) the probe apparatus comprising a probe-body comprising an outer tube and first and second ends; and a cam-twist type interconnect mechanism comprising a male interconnect piece secured to the second end and a female interconnect piece;
  (b) the extender assembly comprising a housing within which a flexible wiring layer extends, the flexible wiring layer in electrical communication with an electrical connector keyed for positioning with a keyed-connector housed within the female interconnect piece;
  (c) a second male interconnect piece located at a first end of the extender assembly for operational association with the female interconnect piece, the second male interconnect piece comprising at least one protuberance outwardly-directed from a second outer cylindrical surface; and
  (d) a second female interconnect piece located at a second end of the extender assembly, the second female interconnect piece having a second cylindrical-section along which a second sleeve having at least one inclined aperture, may slide.

* * * * *

UNITED STATES PATENT AND TRADEMARK OFFICE
CERTIFICATE OF CORRECTION

| | | |
|---|---|---|
| PATENT NO. | : 7,832,295 B2 | Page 1 of 1 |
| APPLICATION NO. | : 11/884352 | |
| DATED | : November 16, 2010 | |
| INVENTOR(S) | : Dustin S. Rodriguez et al. | |

It is certified that error appears in the above-identified patent and that said Letters Patent is hereby corrected as shown below:

Column 7, line 64, "300 or" should read --30 or--;
Column 9, line 43, "adapted, for" should read --adapted for--.

Signed and Sealed this
Eighteenth Day of January, 2011

David J. Kappos
*Director of the United States Patent and Trademark Office*